United States Patent [19]
Hoffman et al.

[11] Patent Number: 6,096,763
[45] Date of Patent: Aug. 1, 2000

[54] $\alpha_{1A}$ ADRENERGIC RECEPTOR ANTAGONISTS

[75] Inventors: Jacob M. Hoffman; Raymond S. L. Chang, both of Lansdale, Pa.

[73] Assignee: Merck & Co., Inc., Rahway, N.J.

[21] Appl. No.: 09/282,743

[22] Filed: Mar. 31, 1999

Related U.S. Application Data

[60] Division of application No. 08/860,314, filed as application No. PCT/US96/02534, Feb. 23, 1996, Pat. No. 5,952,351, which is a continuation-in-part of application No. 08/392,699, Feb. 23, 1995, abandoned
[60] Provisional application No. 60/002,534, Aug. 18, 1995.

[51] Int. Cl.[7] .................................................. A61K 31/445
[52] U.S. Cl. .......................... 514/321; 514/322; 546/198; 546/199
[58] Field of Search ................................... 514/321, 322; 546/198, 199

[56] References Cited

U.S. PATENT DOCUMENTS

| | | | |
|---|---|---|---|
| 3,982,001 | 9/1976 | Heffe et al. | 424/267 |
| 4,066,722 | 1/1978 | Vandenberk et al. | 424/267 |
| 4,110,449 | 8/1978 | Wade et al. | 424/250 |
| 4,470,989 | 9/1984 | Henning et al. | 424/267 |
| 4,980,365 | 12/1990 | Davis | 514/379 |
| 5,008,264 | 4/1991 | Davis | 514/253 |
| 5,064,840 | 11/1991 | Carr et al. | 514/322 |
| 5,141,930 | 8/1992 | Nakao et al. | 514/211 |
| 5,143,923 | 9/1992 | Hrib et al. | 514/321 |
| 5,192,775 | 3/1993 | Malen et al. | 514/321 |
| 5,229,399 | 7/1993 | Malen et al. | 514/321 |
| 5,232,931 | 8/1993 | Prucher et al. | 514/321 |
| 5,262,418 | 11/1993 | Van Daele et al. | 514/258 |
| 5,280,030 | 1/1994 | Jegham et al. | 514/322 |
| 5,371,094 | 12/1994 | Heine et al. | 514/323 |
| 5,403,847 | 4/1995 | Gluchowski et al. | 514/318 |
| 5,462,942 | 10/1995 | Hartog et al. | 514/254 |

FOREIGN PATENT DOCUMENTS

| | | |
|---|---|---|
| 2 621 588 | 4/1989 | France . |
| WO 92/16213 | 10/1992 | WIPO . |
| WO 94/08040 | 4/1994 | WIPO . |
| WO 94/10989 | 5/1994 | WIPO . |
| WO 94/21660 | 9/1994 | WIPO . |
| WO 95/28397 | 10/1995 | WIPO . |
| WO 96/25934 | 8/1996 | WIPO . |

OTHER PUBLICATIONS

Elde et al. "Distribution of neuropeptide receptors . . . " Medline 95336119, 1995.

A. F. Casey, "Opioid Receptors and their Ligands: Recents Developments", Advances in Drug Research, vol. 18, pp. 179–285, (1989).

J. M. Wetzel et al., "Discovery of Alpha 1a Adrenergic Receptor Antagonists based on the L–Type . . . ", Journal of Medicinal Chemistry, vol. 38, No. 10, pp. 1579–1581, (1995).

C. Chapple, "Medical treatment for benign prostatic hyperplasia: surgery still gives the best results", British Medical Journal, vol. 304, No. 6836, p. 1198(2), May 9, 1992.

T. Resine et al., "Opioid Analgesics and Antagonists", Goodman and Gilman's The Pharmaceutical Basis of Therapeutics, pp. 521–555, (1995).

Primary Examiner—Ceila Chang
Attorney, Agent, or Firm—Kenneth R. Walton; Melvin Winokur

[57] ABSTRACT

This invention relates to novel compounds, their synthesis and use as selective $\alpha_{1a}$ adrenergic receptor antagonists. One application of the compounds is in the treatment of benign prostatic hyperplasia. The compounds are selective in their ability to relax smooth muscle tissue enriched in the $\alpha_{1a}$ receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved.

19 Claims, No Drawings

$\alpha_{1A}$ ADRENERGIC RECEPTOR ANTAGONISTS

This application is a divisional of U.S. Ser. No. 08/860,314, filed Aug. 13, 1997, U.S. Pat. No. 5,952,351, which is the national stage of International Application No. PCT/US 96/02534, filed Feb. 23, 1996, which is a continuation-in-part of prior applications U.S. Ser. Nos. 08/392,699, filed Feb. 23, 1995, abandoned, and 60/002,534, filed Aug. 18, 1995, abandoned, the contents of both of which are hereby incorporated by reference.

This invention relates to certain novel compounds, their synthesis, and their use as a selective alpha 1a adrenoceptor antagonists. More particularly, the compounds of the present invention are useful for treating benign prostatic hyperplasia.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in WO 92/0073, the selective ability of the R(+) enantiomer of terazosin to selectively bind to adrenergic receptors of the alpha 1 subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, is limited by their $\alpha_2$ adrenergic receptor mediated induction of increased plasma catecholamine concentration and the attendant physiological sequelae (increased heart rate and smooth muscle contraction).

For a general background on the $\alpha$-adrenergic receptors, the reader's attention is directed to Robert R. Ruffolo, Jr., $\alpha$-*Adrenoreceptors: Molecular Biology, Biochemistry and Pharmacology*, (*Progress in Basic and Clinical Pharmacology* series, Karger, 1991), wherein the basis of $\alpha_1/\alpha_2$ subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting $\alpha$-adrenergic receptor affinity was explored.

The cloning, sequencing and expression of alpha receptor subtypes from animal tissues has led to the subclassification of the $\alpha_1$ receptors into $\alpha_{1a}$, (Lomasney, et al., *J. Biol. Chem.*, 266:6365–6369 (1991), rat $\alpha_{1a}$; Bruno et al., *BBRC*, 179:1485–1490 (1991), human $\alpha_{1a}$), $\alpha_{1b}$ (Cotecchia, et al., *PNAS*, 85;7159–7163 (1988), hamster $\alpha_{1b}$; Libert, et al., *Science,* (1989), dog $\alpha_{1b}$; Ramarao, et al., *J. Biol. Chem.*, 267:21936–21945 (1992), human $\alpha_{1b}$), and most recently, in a study using bovine brain, a new $\alpha_{1c}$ subtype was proposed (Schwinn, et al., *J. Biol. Chem.*, 265:8183–8189 (1990); Hirasawa et al., *BBRC* 195:902–909 (1993), described the cloning, functional expression and tissue distribution of a human $\alpha_{1c}$ adrenergic receptor; Hoehe et al., *Human Mol. Genetics* 1(5):349 (8/92) noted the existence of a two-allele Pst1 restriction fragment polymorphism in the $\alpha_{1c}$ adrenergic receptor gene; another study suggests that there may even be an alpha 1d receptor subtype, see Perez et al., *Mol. Pharm.*, 40:876–883, 1992). Each $\alpha_1$ receptor subtype exhibits its own pharmacologic and tissue specificities. Schwinn and coworkers noted that the cloned bovine $\alpha_{1c}$ receptor exhibited pharmacological properties proposed for the $\alpha_{1a}$ subtype. Nonetheless, based on its non-expression in tissues where the $\alpha_{1a}$ subtype is expressed, and its sensitivity to chloroethylclonidine, the receptor was given a new designation.

The differences in the $\alpha$-adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

In benign prostatic hyperplasia, the male hormone 5$\alpha$-dihydrotestosterone has been identified as the principal culprit. The continual production of 5$\alpha$-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.s' product PROSCAR® (finasteride). The effect of this compound is to inhibit the enzyme testosterone 5-alpha reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the urethral smooth muscle, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/0073, the selective ability of the R(+) enantiomer of terazosin to bind to adrenergic receptors of the $\alpha_1$ subtype was reported. In addition, in WO 92/161213, hereby incorporated by reference, combinations of 5-alpha-reductase inhibitory compounds and alpha 1-adrenergic receptor blockers (terazosin, doxazosin, prazosin, bunazosin, indoramin, alfuzosin) were disclosed. However, no information as to the $\alpha_{1A}$, $\alpha_{1B}$, or $\alpha_{1C}$ subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1a and alpha 1b receptors in the peripheral vasculature, e.g., hypotension and syncope.

Typically, identification of active compounds is accomplished through use of animal tissues known to be enriched in adrenergic receptors. Thus, rat tissues have been used to screen for potential adrenergic receptor antagonists. However, because of species variability, compounds which appear active in animal tissue may not be active or sufficiently selective in humans. This results in substantial wastage of time and effort, particularly where high volume compound screening programs are employed. There is also the danger that compounds, which might be highly effective in humans, would be missed because of their absence of appreciable affinity for the heterologous animal receptors. In this regard, it has been noted that even single amino acid changes between the sequence of biologically active proteins in one species may give rise to substantial pharmacological differences. Thus, Fong et al., (*J. Biol. Chem.*, 267:25668–25671, 1992) showed that there are 22 divergent amino acid residues between the sequence of the human neurokinin-1 receptor and the homologous rat receptor. They further showed, in studies with mutant receptors, that substitution of only two amino acid residues was both necessary and sufficient to reproduce the rat receptor's antagonist binding affinity in the human receptor. Oksenberg et al., (*Nature* 360:161–163, 1992) showed that a single amino-acid difference confers major pharmacological variation between the human and the rodent 5-hydroxytryptamine receptors. Likewise, Kuhse et al., (*Neuron,* 5:867–873, 1990) showed that a single amino-acid exchange alters the pharmacology of the neonatal rat glycine receptor subunit. This difficulty and unpredictability has resulted in a need for a compound screen which will identify compounds that will be active in humans.

These problems were solved by cloning the human adrenergic receptor of the $\alpha_{1c}$ subtype (ATCC CRL 11140) and the use of a screening assay which enables identification of compounds which specifically interact with the human $\alpha_{1c}$ adrenergic receptor. [PCT International Application Publication Nos. WO94/08040, published Apr. 14, 1994 and WO94/10989, published May 26, 1994] As disclosed in the instant patent disclosure, a cloned human $\alpha_{1c}$ adrenergic receptor and a method for identifying compounds which bind the human $\alpha_{1c}$ receptor has now made possible the identification of selective human $\alpha_{1c}$ adrenergic receptor antagonists useful for treating BPH. The instant patent disclosure discloses novel compounds which selectively bind to the human $\alpha_{1c}$ receptor. These compounds are further tested for binding to other human alpha 1 receptor subtypes, as well as counterscreened against other types of receptors, thus defining the specificity of the compounds of the present invention for the human $\alpha_{1c}$ adrenergic receptor.

Compounds of this invention are used to reduce the acute symptoms of BPH. Thus, compounds of this invention may be used alone or in conjunction with a more long-term anti-BPH therapeutics, such as testosterone 5-alpha reductase inhibitors, including PROSCAR® (finasteride). Aside from their utility as anti-BPH agents, these compounds may be used to induce highly tissue-specific, localized $\alpha_{1c}$ adrenergic receptor blockade whenever this is desired. Effects of this blockade include reduction of intra-ocular pressure, control of cardiac arrhythmias, and possibly a host of alpha 1c receptor mediated central nervous system events.

NOMENCLATURE

Recently, a new $\alpha_1$ adrenergic receptor ($\alpha_1$-AR) classification scheme similar to that proposed by Ford, et al. [$\alpha_1$-*Adrenoceptor Classification: Sharpening Occam's Razor, Trends in Pharm. Sci.* 1994, 15, 167–170] was adopted at the August, 1994 meeting of the International Union of Pharmacology (IUPHAR) in Montreal, Canada. The $\alpha_1$-AR genes formerly known as $\alpha_{1a/d}$, $\alpha_{1b}$ and $\alpha_{1c}$ were renamed $\alpha_{1d}$, $\alpha_{1b}$ and $\alpha_{1a}$, respectively. This new naming system reflects the correspondence between the proteins encoded by the $\alpha_{1a}$ and $\alpha_{1b}$ genes (new IUPHAR nomenclature) and the receptors characterized by traditional pharmacological means as $\alpha_{1A}$ and $\alpha_{1B}$, respectively, in the literature. Recombinant receptors and receptors characterized pharmacologically in tissues are distinguished by lowercase and uppercase subscripts, respectively.

The above discussion contained in the Background section used the former classification scheme (i.e., $\alpha_{1a/d}$, $\alpha_{1b}$ and $\alpha_{1c}$); however, hereinafter, the new classification scheme will be utilized (i.e., $\alpha_{1d}$, $\alpha_{1b}$ and $\alpha_{1a}$). Thus, what was formerly referred to as the $\alpha_{1c}$ receptor (and $\alpha_{1c}$ receptor antagonists) will hereinafter be referred to utilizing the new nomenclature as the $\alpha_{1a}$ receptor (and $\alpha_{1a}$ receptor antagonists).

SUMMARY OF THE INVENTION

The present invention provides novel compounds for the treatment of urinary obstruction caused by benign prostatic hyperplasia (BPH). The compounds selectively antagonize the human $\alpha_{1a}$ adrenergic receptor at subnanomolar concentration while exhibiting at least 100 fold lower affinity for the $\alpha_{1d}$ and $\alpha_{1b}$ human adrenergic receptors and many other G-protein coupled receptors. This invention has the advantage over non-selective $\alpha_1$ adrenoceptor antagonists of reduced side effects related to peripheral adrenergic blockade. Such side effects include hypotension, syncope, lethargy, etc. The compounds of the present invention have the structure:

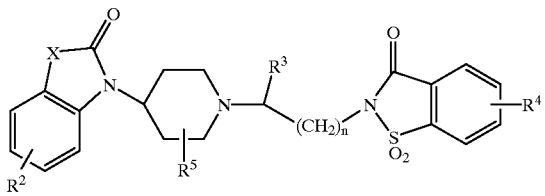

wherein X is selected from N—$R^1$ or O;

$R^1$ is selected from the group consisting of hydrogen, $C_{3-6}$ cycloalkyl, unsubstituted or substituted $C_{1-6}$ alkyl where the substituent on the alkyl is selected from mono-, di- or tri-halogen, $C_{1-4}$ alkoxy, carboxy, $CONH_2$, $SO_2NH_2$, a heterocyclic ring or aryl, and unsubstituted or substituted $C_{2-6}$ alkenyl where the substituent on the alkenyl is selected from mono-, di- or tri-halogen, $C_{1-4}$ alkoxy, carboxy, $CONH_2$, $SO_2NH_2$, a heterocyclic ring or aryl;

$R^2$ is independently one or more of hydrogen, halogen, $C_{1-4}$ alkoxy, mono-, di- or tri-halogenated $C_{1-4}$ alkoxy, or unsubstituted or substituted $C_{1-6}$ alkyl where the substituent on the alkyl is selected from mono-, di- or tri-halogen, $C_{1-4}$ alkoxy, carboxy, $CONH_2$, $SO_2NH_2$, a heterocyclic ring or aryl;

$R^3$ is selected from hydrogen, cyano, $CO_2R^1$, $CONH_2$, $CONHR^1$, $CON(R^1)_2$, $C_{3-6}$ cycloalkyl or $C_{3-6}$ cycloalkyl wherein one of the carbon atoms is replaced with a heteroatom selected from O or NH, or unsubstituted or substituted mono- or di-$C_{1-6}$ alkyl wherein the substituent on the mono- or di-alkyl is selected from hydroxy, $C_{1-4}$ alkoxy, amino or mono-, di- or tri-halogen;

$R^4$ is independently one or more of hydrogen, $C_{1-6}$ alkyl, halogen, $C_{1-4}$ alkoxy, mono-, di- or tri-halogenated $C_{1-4}$ alkoxy, nitro, amino, mono-, di- or tri-halogenated $C_{1-6}$ alkyl, $C_{1-6}$ alkylsulfonyl, $C_{1-4}$ alkylenedioxy, unsubstituted or substituted aryl where the substituent on the aryl is selected from halogen, unsubstituted $C_{1-3}$ alkyl, mono-, di- or tri-halogenated $C_{1-3}$ alkyl or $C_{1-4}$ alkoxy-$C_{1-3}$ alkyl, or unsubstituted or substituted heterocyclic ring where the substituent on the heterocyclic ring is selected from halogen, unsubstituted $C_{1-3}$ alkyl, mono-, di- or tri-halogenated $C_{1-3}$ alkyl or $C_{1-4}$ alkoxy-$C_{1-3}$ alkyl;

$R^5$ is independently one or more of hydrogen, cyano, $C_{1-6}$ alkyl, $CO_2R^1$, $CONH_2$, $CONHR^1$, $CON(R^1)_2$; and n is an integer of from 2 to 4;

provided that when $R^3$ and $R^5$ are both hydrogen, then X is N—$R^1$ where $R^1$ is selected from $C_{3-6}$ cycloalkyl; unsubstituted $C_{2-6}$ alkyl or substituted $C_{1-6}$ alkyl where the substituent on the alkyl is selected from mono-, di- or tri-halogen, $C_{1-4}$ alkoxy, carboxy, $CONH_2$, $SO_2NH_2$, a heterocyclic ring or aryl; or unsubstituted or substituted $C_{2-6}$ alkenyl where the substituent on the alkenyl is selected from mono-, di- or tri-halogen, $C_{1-4}$ alkoxy, carboxy, $CONH_2$, $SO_2NH_2$, a heterocyclic ring or aryl; and the pharmaceutically acceptable salts thereof.

Preferably, $R^2$ is independently one or more of hydrogen, halogen, $C_{1-4}$ alkoxy or unsubstituted or substituted $C_{1-6}$ alkyl where the substituent on the alkyl is selected from mono-, di- or tri-halogen, $C_{1-4}$ alkoxy, carboxy, $CONH_2$, $SO_2NH_2$, a heterocyclic ring or aryl;

$R^4$ is independently one or more of hydrogen, $C_{1-6}$ alkyl, halogen, $C_{1-4}$ alkoxy, nitro, amino, mono-, di- or tri-halogenated $C_{1-6}$ alkyl, $C_{1-6}$ alkylsulfonyl, $C_{1-4}$ alkylenedioxy, unsubstituted or substituted aryl where the substituent on the aryl is selected from halogen, unsubstituted $C_{1-3}$ alkyl, mono-, di- or tri-halogenated $C_{1-3}$ alkyl or $C_{1-4}$ alkoxy-$C_{1-3}$ alkyl, or unsubstituted or substituted heterocyclic ring where the substituent on the heterocyclic ring is selected from halogen, unsubstituted $C_{1-3}$ alkyl, mono-, di- or tri-halogenated $C_{1-3}$ alkyl or $C_{1-4}$ alkoxy-$C_{1-3}$ alkyl; and all other variables are as defined above; provided that when $R^3$ and $R^5$ are both hydrogen, then X is N—$R^1$ where $R^1$ is unsubstituted $C_{2-6}$ alkyl or substituted $C_{1-6}$ alkyl where the substituent on the alkyl is selected from mono-, di- or tri-halogen, $C_{1-4}$ alkoxy, carboxy, $CONH_2$, $SO_2NH_2$, a heterocyclic ring or aryl.

In one embodiment of the invention is the compound wherein $R^1$ is selected from the group consisting of hydrogen, unsubstituted or substituted $C_{1-6}$ alkyl where the substituent on the alkyl is selected from mono-, di- or tri-halogen, $C_{1-4}$ alkoxy, carboxy, $CONH_2$, a heterocyclic ring or phenyl, and unsubstituted or substituted $C_{2-6}$ alkenyl where the substituent on the alkenyl is mono-, di- or tri-halogen;

$R^2$ is independently one, two or three of hydrogen, halogen or $C_{1-6}$ alkyl;

$R^3$ is selected from hydrogen, cyano, $C_{1-4}$ alkoxycarbonyl, $CONH_2$ or unsubstituted or substituted mono- or di-$C_{1-6}$ alkyl wherein the substituent on the mono- or di-alkyl is mono-, di- or tri-halogen;

$R^4$ is independently one, two or three of hydrogen, $C_{1-6}$ alkyl, halogen, $C_{1-4}$ alkoxy, mono-, di- or tri-halogenated $C_{1-4}$ alkoxy, nitro or $C_{1-4}$ alkylenedioxy; and $R^5$ is independently one, two or three of hydrogen, cyano, $C_{1-6}$ alkyl or $CO_2R^1$; and where all other variables are as defined above; provided that when $R^3$ and $R^5$ are both hydrogen, then X is N—$R^1$ where $R^1$ is selected from unsubstituted $C_{2-6}$ alkyl or substituted $C_{1-6}$ alkyl where the substituent on the alkyl is selected from mono-, di- or tri-halogen, $C_{1-4}$ alkoxy, carboxy, $CONH_2$, a heterocyclic ring or phenyl; or unsubstituted or substituted $C_{2-6}$ alkenyl where the substituent on the alkenyl is selected from mono-, di- or tri-halogen; and the pharmaceutically acceptable salts thereof.

Preferably, $R^4$ is independently one, two or three of hydrogen, $C_{1-6}$ alkyl, halogen, $C_{1-4}$ alkoxy, nitro or $C_{1-4}$ alkylenedioxy; and all other variables are as defined above; provided that when $R^3$ and $R^5$ are both hydrogen, then X is N—$R^1$ where $R^1$ is selected from unsubstituted $C_{2-6}$ alkyl or substituted $C_{1-6}$ alkyl where the substituent on the alkyl is selected from mono-, di- or tri-halogen, $C_{1-4}$ alkoxy, carboxy, $CONH_2$, a heterocyclic ring or phenyl.

In a class of the invention is the compound wherein $R^1$ is selected from hydrogen, $C_{1-6}$ alkyl, mono-, di- or tri-halogenated $C_{1-6}$ alkyl, benzyl, $C_{2-6}$ alkenyl or mono-, di- or tri-halogenated $C_{2-6}$ alkenyl;

$R^3$ is selected from hydrogen, cyano or mono- or di-$C_{1-6}$ alkyl; and $R^4$ is independently one, two or three of hydrogen, $C_{1-6}$ alkyl, halogen, $C_{1-4}$ alkoxy, mono-, di- or tri-halogenated $C_{1-4}$ alkoxy or $C_{1-4}$ alkylenedioxy; and where all other variables are as defined above; provided that when $R^3$ and $R^5$ are both hydrogen, then X is N—$R^1$ where $R^1$ is selected from unsubstituted $C_{2-6}$ alkyl, mono-, di- or tri-halogenated $C_{1-6}$ alkyl, benzyl, $C_{2-6}$ alkenyl or mono-, di- or tri-halogenated $C_{2-6}$ alkenyl; and the pharmaceutically acceptable salts thereof.

Preferably, $R^4$ is independently one, two or three of hydrogen, $C_{1-6}$ alkyl, halogen or $C_{1-4}$ alkylenedioxy; and all other variables are as defined above; provided that when $R^3$ and $R^5$ are both hydrogen, then X is N—$R^1$ where $R^1$ is selected from unsubstituted $C_{2-6}$ alkyl, mono-, di- or tri-halogenated $C_{1-6}$ alkyl or benzyl.

In a subclass of the invention is the compound of the formula

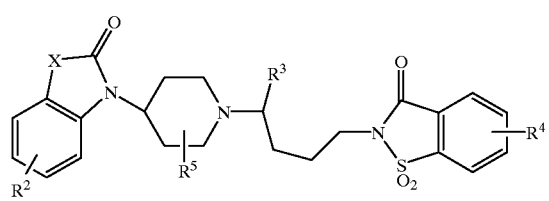

wherein $R^1$ is selected from hydrogen, $C_{1-4}$ alkyl, $C_{2-6}$ alkenyl, benzyl, trifluoroethyl or fluoroethyl;

$R^2$ is selected from hydrogen, chlorine, fluorine or methyl; and $R^3$ is selected from hydrogen, methyl or dimethyl;

$R^4$ is selected from hydrogen, chlorine, ethoxy, trifluoromethoxy or ethylenedioxy; and $R^5$ is selected from hydrogen, cyano, methyl or methoxycarbonyl; and where all other variables are as defined above; provided that when $R^3$ and $R^5$ are both hydrogen, then X is N—$R^1$ where $R^1$ is selected from unsubstituted $C_{2-4}$ alkyl, $C_{2-6}$ alkenyl, benzyl, trifluoroethyl or fluoroethyl; and the pharmaceutically acceptable salts thereof.

Preferably, $R^4$ is independently one or more of hydrogen, chlorine or ethylenedioxy; and all other variables are as defined above; provided that when $R^3$ and $R^5$ are both hydrogen, then X is N—$R^1$ where $R^1$ is selected from unsubstituted $C_{2-4}$ alkyl, $C_{2-6}$ alkenyl, benzyl, trifluoroethyl or fluoroethyl.

Illustrative of the invention is the compound of the formula

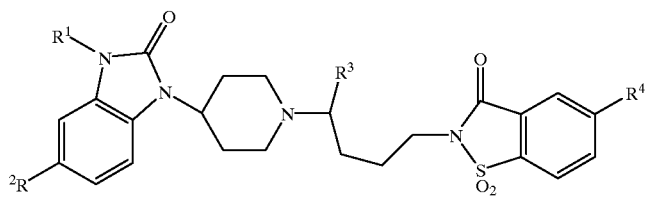

where all other variables are as defined above; provided that when $R^3$ is hydrogen, then $R^1$ is selected from unsubstituted $C_{2-4}$ alkyl, $C_{2-6}$ alkenyl, benzyl, trifluoroethyl or fluoroethyl; and the pharmaceutically acceptable salts thereof.

An illustration of the invention is the compound of the formula

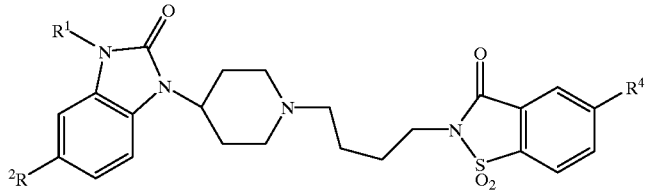

wherein $R^1$ is selected from ethyl, trifluoroethyl or fluoroethyl;

$R^2$ is selected from chlorine, fluorine or methyl; and $R^4$ is selected from hydrogen, chlorine, ethoxy, methoxy or trifluoromethoxy; and the pharmaceutically acceptable salts thereof.

Exemplifying the invention is the compound selected from:
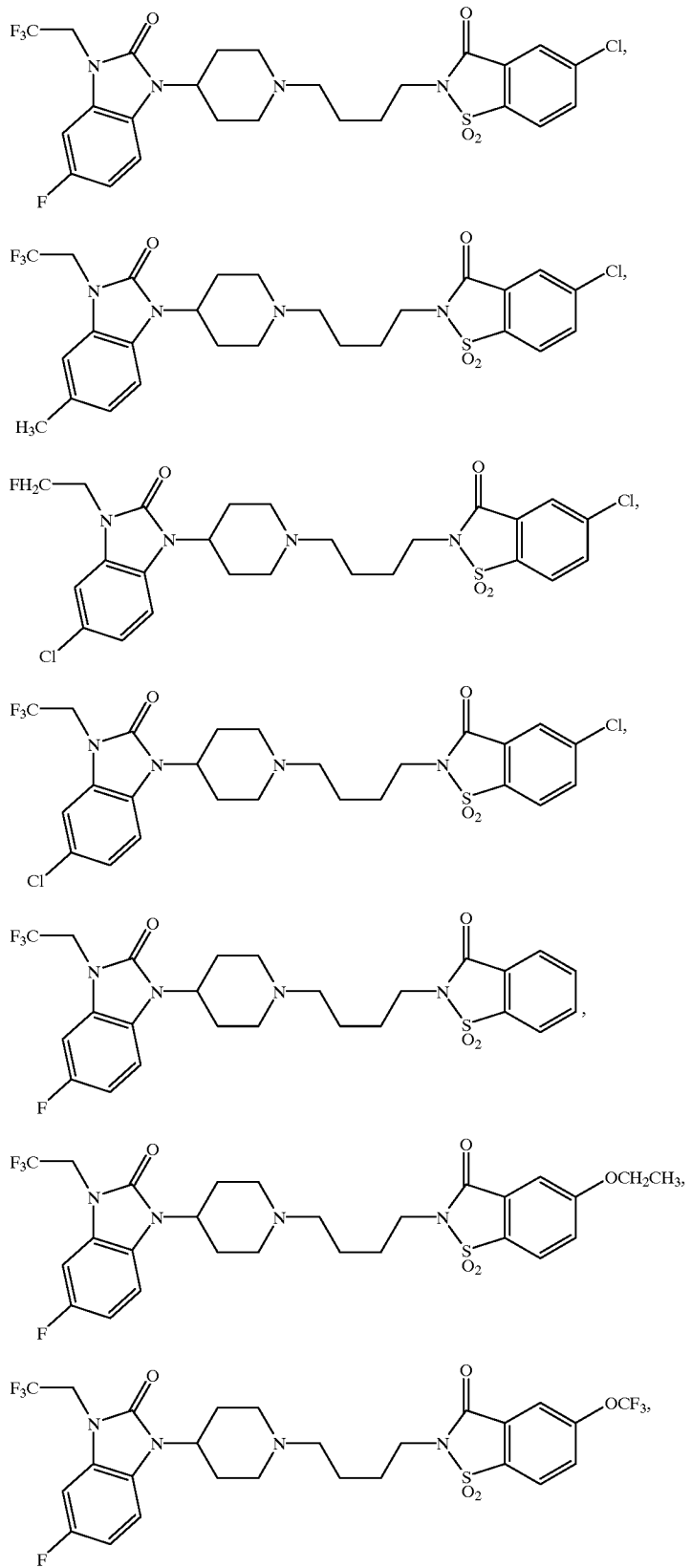

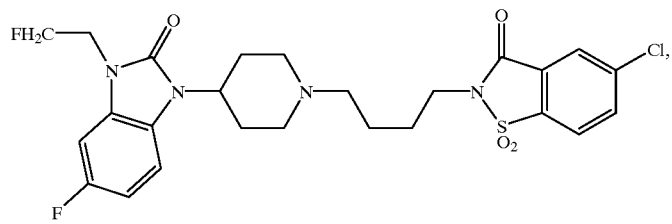
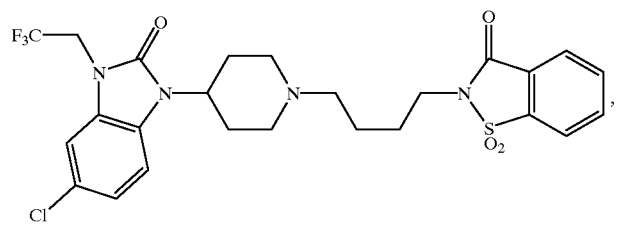
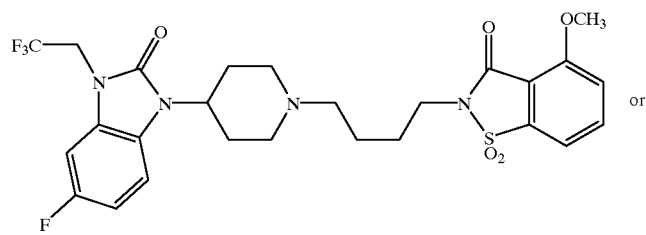
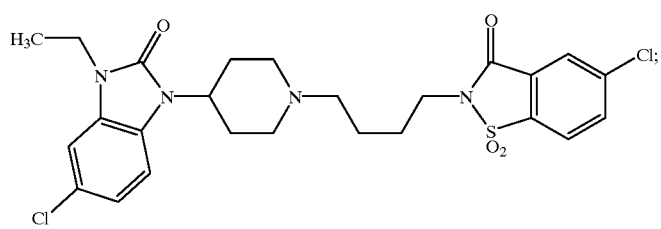
and the pharmaceutically acceptable salts thereof.
An example of the invention is the compound selected from
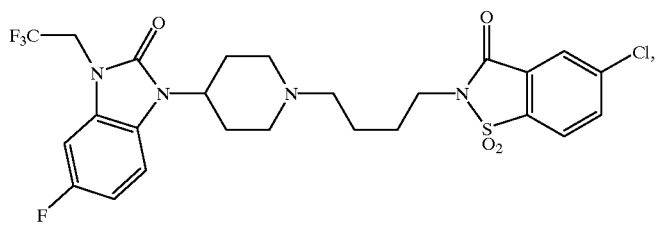
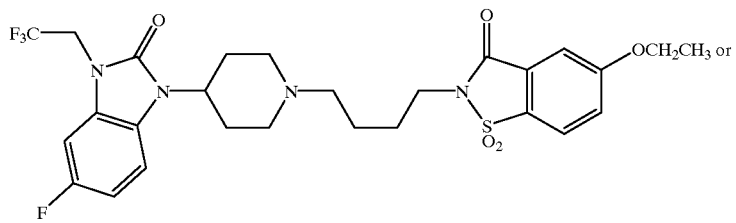

-continued

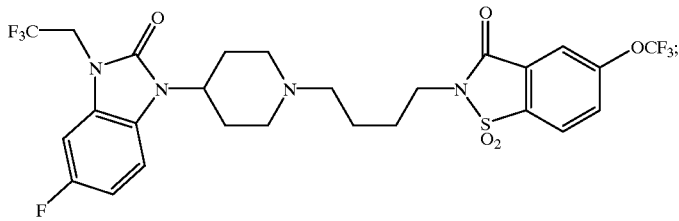

and the pharmaceutically acceptable salts thereof.

Further illustrating the invention is a pharmaceutical composition comprising a therapeutically effective amount of any of the compounds described above and a pharmaceutically acceptable carrier.

Further exemplifying the invention is the composition further comprising a therapeutically effective amount of a testosterone 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

Another illustration of the invention is a method of treating benign prostatic hyperplasia, relaxing urethral smooth muscle, relaxing prostatic smooth muscle and/or improving urine flow in a subject in need thereof which comprises administering to the subject a therapeutically effective amount of any of the compounds or any of the pharmaceutical compositions described above.

More particularly illustrating the invention are the methods of treating BPH, relaxing urethral smooth muscle, relaxing prostatic smooth muscle and/or improving urine flow wherein the compound or pharmaceutical composition additionally does not cause a fall in blood pressure at dosages effective to alleviate BPH, relax urethral smooth muscle, relax prostatic smooth muscle and/or improve urine flow.

Additional illustrations of the invention are the methods of treating benign prostatic hyperplasia, relaxing urethral smooth muscle, relaxing prostatic smooth muscle and improving urine flow wherein the compound is administered in combination with a testosterone 5-alpha reductase inhibitor. Preferably, the testosterone 5-alpha reductase inhibitor is a type 1, a type 2, both a type 1 and a type 2 or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

More specifically exemplifying the invention is a method of treating a disease which is susceptible to treatment by antagonism of the alpha 1a adrenergic receptor which comprises administering to a subject in need thereof an amount of any of the compounds or pharmaceutical compositions described above effective to treat the disease. Diseases which are susceptible to treatment by antagonism of the alpha 1a receptor include, but are not limited to, BPH, high intraocular pressure, glaucoma, high cholesterol, impotency, sympathetically mediated pain and cardiac arrhythmia.

An additional example of the invention is a drug which is useful for treating BPH, relaxing urethral smooth muscle, relaxing prostatic smooth muscle and/or improving urine flow in a mammal in need thereof, the effective ingredient of the said drug being any of the compounds descibed above.

More specifically illustrating the invention is the use of any of the compounds described above in the preparation of a medicament for the treatment of BPH, relaxing urethral smooth muscle, relaxing prostatic smooth muscle and/or improving urine flow in a mammal in need thereof.

Another aspect of the invention is a method of preparing any of the compounds described above which comprises alkylating a halogenated butyl saccharin with a deprotected benzimidazolyl piperidine or a deprotected benzoxazolinyl piperidine. Preferably, the method comprises reacting a butyl saccharin moiety with a piperidinylbenzimidazolinone moiety.

DETAILED DESCRIPTION OF THE INVENTION

The compounds of the present invention exhibit high selectivity for the human alpha 1a adrenergic receptor. One implication of this selectivity is that the compounds display selectivity for lowering intraurethral pressure without substantially affecting diastolic blood pressure. The compounds of the present invention are useful for relaxing urethral smooth muscle; additionally, the compounds claimed herein are useful for relaxing prostatic smooth muscle. The ability of the compounds of the present invention to relax urethral and prostatic smooth muscle results in improved urine flow in patients suffering from impaired urine flow (i.e., difficulty in urination) due to enlargement of the prostate gland. Thus, the compounds of the present invention are useful for treating BPH.

Representative compounds of this invention display submicromolar affinity for the human $\alpha_{1a}$ adrenergic receptor subtype while displaying at least ten-fold lower affinity for the human $\alpha_{1d}$ and $\alpha_{1b}$ adrenergic receptor subtypes, and many other G-protein coupled human receptors. Particular representative compounds of this invention exhibit nanomolar and subnanomolar affinity for the human $\alpha_{1a}$ adrenergic receptor subtype while displaying at least 30 fold lower affinity for the human $\alpha_{1d}$ and $\alpha_{1b}$ adrenergic receptor subtypes, and many other G-protein coupled human receptors. The most preferred compounds of this invention exhibit a Ki for human $\alpha_{1a}$ adrenergic receptors which is more than 100 fold lower than for the human $\alpha_{1d}$ or $\alpha_{1b}$ adrenergic receptors, while exhibiting greater than 50 fold selectivity for the human $\alpha_{1a}$ adrenergic receptor over all other human G-protein coupled receptors tested (including serotonin, dopamine, alpha 2 adrenergic, beta adrenergic or muscarinic receptors).

Representative compounds of the present invention are also potent opioid agonists useful as analgesics to eliminate or ameliorate pain and suffering in animals, preferably mammals, especially humans, without loss of consciousness. More particularly, the opioid agonist compounds described herein are selective for the mu opioid receptor over the kappa and delta opioid receptors.

Opioids are a class of drugs which are, to varying degrees, opium-like or morphine-like in their properties. The opium group of narcotic drugs are among the most powerfully acting and clinically useful drugs producing depression of the central nervous system (CNS). Drugs of this group are used principally as analgesics, but possess numerous other useful properties. Morphine, for example, is used to induce sleep in the presence of pain, relieve diarrhea, suppress cough, ease dyspnea and facilitate anesthesia.

Analgesia is defined as the reduction of awareness of pain and suffering without loss of consciousness. Analgesic compounds are agents which produce a state of analgesia, and thus, analgesics are compounds which alleviate and are useful for treating pain without loss of consciousness.

By the year 1967, researchers working in the art had concluded that the complex interactions in the body between morphine agonists (morphine-like drugs) and mixed morphine agonist-antagonists could best be explained by postulating the existence of more than one type of cellular receptor for the opioids, and for related drugs.

Subsequent research in the area has revealed that multiple categories of opioid receptors exist and that there are at least three distinct families of opioid peptides, the endorphins, the enkephalins and the dynorphans. Although studies of the binding of opioid drugs and peptides to specific sites in brain and other organs has suggested the existence of perhaps as many as eight different types of opioid receptors in the body, there is reasonably firm evidence supporting the existence of three major categories of opioid receptors, designated mu, kappa and delta, in the CNS.

The multiplicity of opioid receptor types in the CNS is now well established. Yet, although much work has been directed at defining the structural elements that determine receptor specificity and efficacy, these factors are still poorly understood.

The rigid alkaloid opiates, typified by morphine, are believed to produce their major effects on the CNS and the bowel by acting as agonists, particularly at the mu receptors; however, morphine also has appreciable affinity for kappa and delta receptors. [Jaffe, J. H.; Martin, W. R., *Opioid Analgesics and Antagonists*, in Goodman & Gilman's *The Pharmacological Basis of Therapeutics* (8th ed. 1990)]. Although there is evidence that mu receptors are linked to the development of physical dependence, at least one researcher (Pasternak (1986)) believes that the withdrawal syndrome is associated with a variety of receptor subtypes [Casy, A. F., *Opioid Receptors and their Ligands: Recent Developments*, in *Advances in Drug Research, Vol. 18* (1989)].

It is believed that ligands which are highly selective for a single opioid receptor type or subtype have the potential of minimizing or eliminating unwanted side effects mediated by the other opioid receptor types. It has now been found that compounds of the present invention are highly selective for the mu opioid receptor and are therefore useful as analgesic agents. In addition, although opioid agonists are primarily employed as analgesics, the compounds described herein are also useful as antitussives, antidiarrhea agents, anesthetics and tranquilizers.

Thus, in another aspect of the invention is a method of treating a condition which is susceptible to treatment by agonism of a mu opioid receptor which comprises administering to a subject in need thereof an amount of a compound effective to treat the condition wherein the compound has the formula:

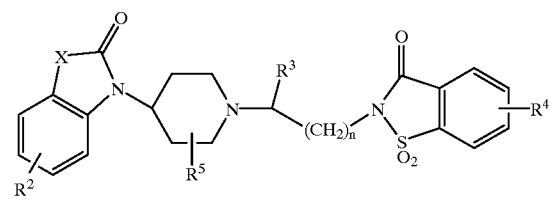

wherein X is selected from N—$R^1$ or O;

$R^1$ is selected from the group consisting of hydrogen, $C_{3-6}$ cycloalkyl, unsubstituted or substituted $C_{1-6}$ alkyl where the substituent on the alkyl is selected from mono-, di- or tri-halogen, $C_{1-4}$ alkoxy, carboxy, $CONH_2$, $SO_2NH_2$, a heterocyclic ring or aryl, and unsubstituted or substituted $C_{2-6}$ alkenyl where the substituent on the alkenyl is selected from mono-, di- or tri-halogen, $C_{1-4}$ alkoxy, carboxy, $CONH_2$, $SO_2NH_2$, a heterocyclic ring or aryl;

$R^2$ is independently one or more of hydrogen, halogen, $C_{1-4}$ alkoxy, mono-, di- or tri-halogenated $C_{1-4}$ alkoxy or unsubstituted or substituted $C_{1-6}$ alkyl where the substituent on the alkyl is selected from mono-, di- or tri-halogen, $C_{1-4}$ alkoxy, carboxy, $CONH_2$, $SO_2NH_2$, a heterocyclic ring or aryl;

$R^3$ is selected from hydrogen, cyano, $CO_2R^1$, $CONH_2$, $CONHR^1$, $CON(R^1)_2$, $C_{3-6}$ cycloalkyl, $C_{3-6}$ cycloalkyl wherein one of the carbon atoms is replaced with a heteroatom selected from O or NH, or unsubstituted or substituted mono- or di-$C_{1-6}$ alkyl wherein the substituent on the mono- or di-alkyl is selected from hydroxy, $C_{1-4}$ alkoxy, amino or mono-, di- or tri-halogen;

$R^4$ is independently one or more of hydrogen, $C_{1-6}$ alkyl, halogen, $C_{1-4}$ alkoxy, mono-, di- or tri-halogenated $C_{1-4}$ alkoxy, nitro, amino, mono-, di- or tri-halogenated $C_{1-6}$ alkyl, $C_{1-6}$ alkylsulfonyl, $C_{1-4}$ alkylenedioxy, unsubstituted or substituted aryl where the substituent on the aryl is selected from halogen, unsubstituted $C_{1-3}$ alkyl, mono-, di- or tri-halogenated $C_{1-3}$ alkyl or $C_{1-4}$ alkoxy-$C_{1-3}$ alkyl, or unsubstituted or substituted heterocyclic ring where the substituent on the heterocyclic ring is selected from halogen, unsubstituted $C_{1-3}$ alkyl, mono-, di- or tri-halogenated $C_{1-3}$ alkyl or $C_{1-4}$ alkoxy-$C_{1-3}$ alkyl;

$R^5$ is independently one or more of hydrogen, cyano, $C_{1-6}$ alkyl, $CO_2R^1$, $CONH_2$, $CONHR^1$, $CON(R^1)_2$; and n is an integer of from 2 to 4;

and the pharmaceutically acceptable salts thereof.

In one embodiment of this aspect of the invention is a method of alleviating pain in a subject in need thereof which comprises administering to the subject a therapeutically effective amount of the compound described above.

In a class of this aspect of the invention is the method of alleviating pain wherein $R^3$ is selected from cyano, $CO_2R^1$, $CONH_2$, $CONHR^1$, $CON(R^1)2$, $C_{3-6}$ cycloalkyl, $C_{3-6}$ cycloalkyl wherein one of the carbon atoms is replaced with a heteroatom selected from O or NH, or unsubstituted or substituted mono- or di-$C_{1-6}$ alkyl wherein the substituent on the mono- or di-alkyl is selected from hydroxy, $C_{1-4}$ alkoxy, amino or mono-, di- or tri-halogen; and $R^4$ is independently one or more of hydrogen, $C_{1-6}$ alkyl, halogen, $C_{1-4}$ alkoxy, mono-, di- or tri-halogenated $C_{1-4}$ alkoxy, nitro or $C_{1-4}$ alkylenedioxy; and wherein all other variables are as defined above; and the pharmaceutically acceptable salts thereof.

In a subclass of this aspect of the invention is the method of alleviating pain wherein $R^1$ is selected from the group consisting of hydrogen, unsubstituted or substituted $C_{1-6}$ alkyl where the substituent on the alkyl is selected from mono-, di- or tri-halogen, $C_{1-4}$ alkoxy, carboxy, $CONH_2$, a heterocyclic ring or phenyl, and unsubstituted or substituted $C_{2-6}$ alkenyl where the substituent on the alkenyl is mono-, di- or tri-halogen;

$R^2$ is independently one or more of hydrogen, halogen or $C_{1-6}$ alkyl;

$R^3$ is selected from cyano, $C_{1-4}$ alkoxycarbonyl, $CONH_2$ or unsubstituted or substituted mono- or di-$C_{1-6}$ alkyl wherein the substituent on the mono- or di-alkyl is mono-, di- or tri-halogen;

$R^4$ is independently one or more of hydrogen or halogen; and $R^5$ is independently one or more of hydrogen, cyano, $C_{1-6}$ alkyl or $CO_2R^1$; and wherein all other variables are as defined above; and the pharmaceutically acceptable salts thereof.

Illustrative of this aspect of the invention is the method of alleviating pain wherein $R^1$ is selected from hydrogen, $C_{1-6}$ alkyl, mono-, di- or tri-halogenated $C_{1-6}$ alkyl, benzyl, $C_{2-6}$ alkenyl or mono-, di- or tri-halogenated $C_{2-6}$ alkenyl;

$R^3$ is selected from cyano or mono- or di-$C_{1-6}$ alkyl; and $R^4$ is independently one or more of hydrogen or chlorine; and wherein all other variables are as defined above; and the pharmaceutically acceptable salts thereof.

An illustration of this aspect of the invention is the method of alleviating pain wherein the compound has the formula

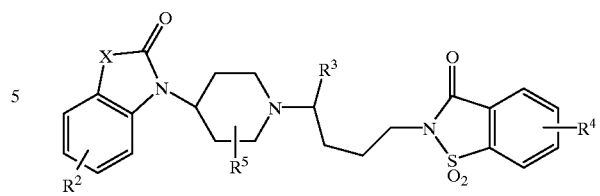

wherein $R^1$ is selected from hydrogen, $C_{1-4}$ alkyl, $C_{2-6}$ alkenyl, benzyl, trifluoroethyl or fluoroethyl;

$R^2$ is independently one or more of hydrogen, chlorine, fluorine or methyl; and $R^3$ is selected from hydrogen, methyl or dimethyl; and $R^5$ is independently one or more of hydrogen, cyano, methyl or methoxycarbonyl; and wherein all other variables are as defined above;

and the pharmaceutically acceptable salts thereof.

Exemplifying this aspect of the invention is the method of alleviating pain wherein the compound has the formula

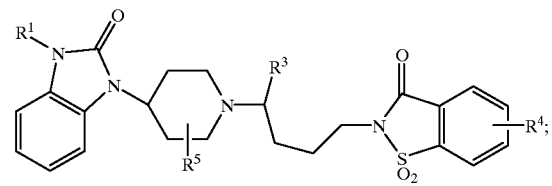

and wherein all variables are as defined above; and the pharmaceutically acceptable salts thereof.

An example of this aspect of the invention is the method of alleviating pain wherein the compound is selected from the group consisting of 1,1-dioxido-2-(4-(4-(3-propyl-2-oxo-1-benzimidazolinyl) piperidin-1-yl)butyl)-5-chloro-1,2-benzisothiazol-3-(2H)-one;

1,1-dioxido-2-(4-(4-(3-ethyl-2-oxo-1-benzimidazolinyl) piperidin-1-yl)pentyl)-1,2-benzisothiazol-3(2H)-one;

1,1-dioxido-2-(4-(4-(3-ethyl-2-oxo-1-benzimidazolinyl) piperidin-1-yl)4-methylpentyl)-1,2-benzisothiazol-3 (2H)-one;

1,1-dioxido-2-(4-(4-(3-ethyl-2-oxo-1-benzimidazolinyl) piperidin-1-yl)butyl)-1,2-benzisothiazol-3(2H)-one;

1,1-dioxido-2-(4-(4-(3-(2,2,2-trifluoroethyl)-2-oxo-1-benzimidazolinyl)piperidin-1-yl)butyl)-1,2-benzisothiazol-3(2H)-one;

1,1-dioxido-2-(4-(4-(3-n-propyl-2-oxo-1-benzimidazolinyl) piperidin-1-yl)butyl)-1,2-benzisothiazol-3(2H)-one;

1,1-dioxido-2-(4-(4-(3-benzyl-2-oxo-1-benzimidazolinyl) piperidin-1-yl)butyl)-1,2-benzisothiazol-3(2H)-one;

1,1-dioxido-2-(4-(4-(3-ethyl-2-oxo-1-benzimidazolinyl) piperidin-1-yl)butyl-5-chloro-1,2-benzisothiazol-3(2H)-one;

1,1-dioxido-2-(4-(4-(3-(2-fluoroethyl)-2-oxo-1-benzimidazolinyl)piperidin-1-yl)butyl-5-chloro-1,2-benzisothiazol-3(2H)-one;

1,1-dioxido-2-(4-(4-(3-ethyl-2-oxo-1-benzimidazolinyl) piperidin-1-yl)butyl)-4,5-ethylenedioxy-1,2-benzisothiazol-3(2H)-one;

1,1-dioxido-2-(4-(4-(5-methyl-3-ethyl-2-oxo-1-benzimidazolinyl)piperidin-1-yl)butyl)-5-chloro-1,2-benzisothiazol-3(2H)-one;

1,1-dioxido-2-(4-(4-(2-oxo-1-benzimidazolinyl)piperidin-1-yl)-4-methylpentyl)-1,2-benzisothiazol-3(2H)-one;

1,1-dioxido-2-(4-(4-(2-oxo-1-benzimidazolinyl)piperidin-1-yl)pentyl)-1,2-benzisothiazol-3(2H)-one;

1,1-dioxido-2-(4-(4-(3-isopropyl-2-oxo-1-benzimidazolinyl)piperidin-1-yl)butyl)-5-chloro-1,2-benzisothiazol-3(2H)-one;

1,1-dioxido-2-(4-(4-(3-butyl-2-oxo-1-benzimidazolinyl)piperidin-1-yl)butyl)-5-chloro-1,2-benzisothiazol-3(2H)-one;

1,1-dioxido-2-(4-(4-(3-(2,2,2-trifluoroethyl)-2-oxo-1-benzimidazolinyl)piperidin-1-yl)butyl)-5-chloro-1,2-benzisothiazol-3(2H)-one;

1,1-dioxido-2-(4-(4-(2-oxo-3-benzoxazolinyl)piperidin-1-yl)pentyl)-1,2-benzisothiazol-3(2H)-one;

1,1-dioxido-2-(4-(4-(6-methyl-2-oxo-3-benzoxazolinyl)piperidin-1-yl)pentyl)-1,2-benzisothiazol-3(2H)-one;

1,1-dioxido-2-(4-(4-(-2-oxo-3-benzoxazolinyl)-2-methylpiperidin-1-yl)butyl)-1,2-benzisothiazol-3(2H)-one;

1,1-dioxido-2-(4-(4-(2-oxo-1-benzimidazolinyl)-3-methoxycarbonyl-piperidin-1-yl)butyl)-5-chloro-1,2-benzisothiazol-3(2H)-one;

1,1-dioxido-2-(4-(4-(5-fluoro-3-ethyl-2-oxo-1-benzimidazolinyl)piperidin-1-yl)butyl)-5-chloro-1,2-benzisothiazol-3(2H)-one;

1,1-dioxido-2-(4-(2-cyano-4-(3-propyl-2-oxo-1-benzimidazolinyl) piperidin-1-yl)butyl)-5-chloro-1,2-benzisothiazol-3(2H)-one; and 1,1-dioxido-2-(4-(4-(3-n-propyl-2-oxo-1-benzimidazolinyl)piperidin-1-yl)pentyl)-5-chloro-1,2-benzisothiazol-3(2H)-one; and the pharmaceutically acceptable salts thereof.

Preferably, the compound is selected from 1,1-dioxido-2-(4-(4-(2-oxo-1-benzimidazolinyl)piperidin-1-yl)pentyl)-1,2-benzisothiazol-3(2H)-one;

1,1-dioxido-2-(4-(4-(3-ethyl-2-oxo-1-benzimidazolinyl)piperidin-1-yl)pentyl)-1,2-benzisothiazol-3(2H)-one;

1,1-dioxido-2-(4-(4-(3-n-propyl-2-oxo-1-benzimidazolinyl)piperidin-1-yl)pentyl)-5-chloro-1,2-benzisothiazol-3(2H)-one;

1,1-dioxido-2-(4-(4-(3-ethyl-2-oxo-1-benzimidazolinyl)piperidin-1-yl)4-methylpentyl)-1,2-benzisothiazol-3(2H)-one; or 1,1-dioxido-2-(4-(4-(2-oxo-1-benzimidazolinyl)piperidin-1-yl)-4-methylpentyl)-1,2-benzisothiazol-3(2H)-one; and the pharmaceutically acceptable salts thereof.

Most preferably, the compound is selected from 1,1-dioxido-2-(4-(4-(3-ethyl-2-oxo-1-benzimidazolinyl)piperidin-1-yl)4-methylpentyl)-1,2-benzisothiazol-3(2H)-one;

1,1-dioxido-2-(4-(4-(2-oxo-1-benzimidazolinyl)piperidin-1-yl)-4-methylpentyl)-1,2-benzisothiazol-3(2H)-one; or 1,1-dioxido-2-(4-(4-(3-ethyl-2-oxo-1-benzimidazolinyl)piperidin-1-yl)pentyl)-1,2-benzisothiazol-3(2H)-one; and the pharmaceutically acceptable salts thereof.

Further illustrating this aspect of the invention is a method of inducing analgesia in a subject in need thereof which comprises administering to the subject a therapeutically effective amount of any of the compounds described above.

Another illustration of this aspect of the invention is a drug which is useful for alleviating pain or inducing analgesia in a mammal in need thereof, the effective ingredient of the said drug being any of the compounds descibed above.

More specifically exemplifying this aspect of the invention is the use of any of the compounds described above in the preparation of a medicament for alleviating pain or inducing analgesia in a mammal in need thereof.

The compounds of the present invention are administered in dosages effective to antagonize the alpha 1a receptor where such treatment is needed, as in BPH, or in dosages effective to agonize the mu opioid receptor where such treatment for pain is needed. For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochoride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbroniide, Methylnitrate, Methylsulfate, Mucate, Napsylate, Nitrate, N-methylglucamine ammonium salt, Oleate, Oxalate, Pamoate (Embonate), Palmnitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water or common organic solvents. Such solvates are also encompassed within the scope of this invention.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "aryl" shall mean phenyl, napthyl or fluorenyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally.

In the compounds of the present invention, the substituents on the piperidine ring (i.e., $R^5$) and the fused benzene rings of the benzimidazolone (or benzoxazolinone) and saccharin rings, i.e., $R^2$ and $R^4$, respectively, can be one or more of the named substituents. That is, the piperidine ring and the benzene rings can be mono-, di-, tri- or tetra-substituted by any of the substituents listed in the definitions of $R^2$, $R^4$ and $R^5$. Moreover, where the piperidine or benzene rings are poly-substituted, the substitutents can be the same or different.

The term heterocycle or heterocyclic ring, as used herein, represents an unsubstituted or substituted stable 5- to 7-membered monocyclic ring system which may be saturated or unsaturated, and which consists of carbon atoms and from one to three heteroatoms selected from N—$R^6$ ($R^6$ is hydrogen, $C_{1-6}$ alkyl or absent), O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

As used herein, in the definition of $R^3$, the term "mono- or di-$C_{1-6}$ alkyl" shall mean that the $R^3$ bound carbon can be mono- or di-substituted with a $C_{1-6}$ alkyl group. Thus, for example, when $R^3$ is dimethyl, then

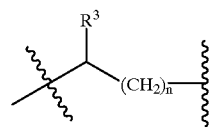

shall mean

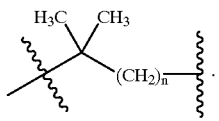

Moreover, when $R^3$ is di-$C_{1-6}$ alkyl, the $C_{1-6}$ alkyl groups can be the same or different.

Similarly, in the definition of $R^3$, the term "$C_{3-6}$ cycloalkyl" shall mean that the methylene group and the $R^3$ substituent can together form a $C_{3-6}$ cycloalkyl ring. Thus, for example, when $R^3$ is cyclopentyl, then

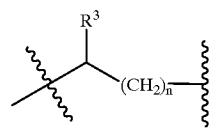

shall mean

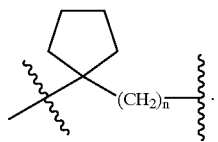

As used herein, in the definition of $R^4$, the term "$C_{1-4}$ alkylenedioxy" shall mean that phenyl ring containing the $R^4$ substituent contains a $C_{1-4}$ alkylenedioxy bridge connecting two adjacent carbon atoms of the benzene ring. Thus, for example, when $R^4$ is ethylenedioxy, then

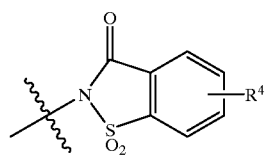

shall mean

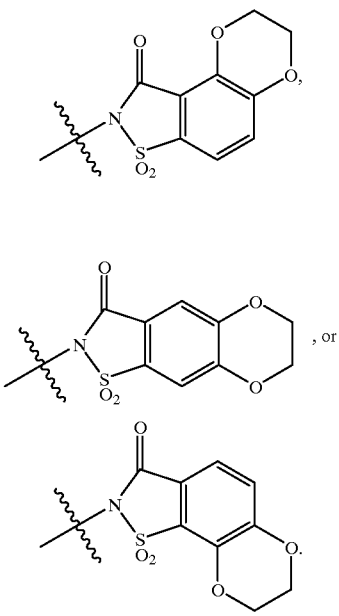

The term "analgesia," as used herein is defined as the reduction of awareness of pain and suffering without loss of consciousness. Analgesic compounds are agents which produce a state of analgesia (i.e., induce analgesia), and thus, analgesics are compounds which alleviate and are useful for treating pain without loss of consciousness.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry,* ed. J. F. W. McOmie, Plenum Press, 1973; and T. W. Greene & P. G. M. Wuts, *Protective Groups in Organic Synthesis,* John Wiley & Sons, 1991. The protecting groups may be removed at a convenient subsequent stage using methods known from the art.

The specificity of binding of compounds showing affinity for the $\alpha_{1a}$ receptor is shown by comparing affinity to membranes obtained from tranfected cell lines that express the $\alpha_{1a}$ receptor and membranes from cell lines or tissues known to express other types of alpha (e.g., $\alpha_{1d}$, $\alpha_{1b}$) or beta adrenergic receptors. Expression of the cloned human $\alpha_{1d}$, $\alpha_{1b}$, and $\alpha_{1a}$ receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the $\alpha_{1a}$ receptor makes them useful for the treatment of BPH. The specificity of binding of compounds showing affinity for the $\alpha_{1a}$ receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994, each of which is hereby incorporated by reference. The cloned human $\alpha_{1a}$ receptor, when expressed in mammalian cell lines, is used to discover ligands that bind to the receptor and alter its function. Expression of the cloned human $\alpha_{1d}$, $\alpha_{1b}$, and $\alpha_{1a}$ receptors and comparison of their binding properties with known selective antagonists provides a rational way for selection of compounds and discovery of new compounds with predictable pharmacological activities.

Compounds of this invention exhibiting selective human $\alpha_{1a}$ adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994 and U.S. Pat. No. 5,403,847, issued Apr. 4, 1995, the contents of which are hereby incorporated by reference]. Compounds which are both selective amongst the various human alpha 1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha 1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors and/or in the alleviation of pain can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician, veterinarian or clinician of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyleneoxidepolylysine substituted with palnitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required and/or whenever relief from pain is required.

The daily dosage of the products may be varied over a wide range from 0.01 to 1,000 mg per adult human/per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 250 mg/kg of body weight per day. Preferably, the range is from about 0.001 to 100 mg/kg of body weight per day, and especially from about 0.001 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human $\alpha_{1a}$ adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-$\alpha$ reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example, hereby incorporated by reference). In addition to PROSCAR®, which is principally active in prostatic tissue due to its selectivity for human 5-$\alpha$ reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5$\alpha$-reductase inhibitors have been described in WO93/23420, EP 0572166; WO 93/23050; WO93123038,; WO93/23048; WO93/23041; WO93/23040; WO93/23039; WO93/23376; WO93/23419, EP 0572165; WO93/23051, each of which is hereby incorporated by reference.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor may be independently optimized and combined to achieve a result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject in the combination is about 0.01 mg per subject per day to about 50 mg per subject per day in combination with an $\alpha_{1a}$ antagonist. Preferably, the dosage of finasteride in the combination is about 0.2 mg per subject per day to about 10 mg per subject per day, more preferably, about 1 to about 7 mg per subject to day, most perferably, about 5 mg per subject per day.

For the treatment of benign prostatic hyperplasia, compounds of this invention exhibiting alpha 1a adrenergic receptor blockade can be combined with a therapeutically effective amount of a 5$\alpha$-reductase 2 inhibitor, such finasteride, in addition to a 5$\alpha$-reductase 1 inhibitor, such as 4,7$\beta$-dimethyl-4-aza-5$\alpha$-cholestan-3-one, in a single oral, systemic, or parenteral pharmaceutical dosage formulation. Alternatively, a combined therapy can be employed wherein the alpha 1a adrenergic receptor antagonist and the 5$\alpha$-reductase 1 or 2 inhibitor are administered in separate oral, systemic, or parenteral dosage formulations. See, e.g., U.S. Pat. Nos. 4,377,584 and 4,760,071 which describe dosages and formulations for 5$\alpha$-reductase inhibitors.

Abbreviations used in the instant specification, particularly the Schemes and Examples, are as follows:

Boc or BOC=t-butyloxycarbonyl
Cbz-Cl=benzyloxycarbonyl chloride
DMF=dimethylformamide
Et=ethyl
$Et_3N$=triethylamine
EtOAc=ethyl acetate
EtOH=ethanol
HPLC=high performance liquid chromatography
HOAc=acetic acid
i-PrOH=isopropanol
Me=methyl
MeOH=methanol
mp=melting point
NMR=nuclear magnetic resonance
PEI=polyethylenimine
Ph=phenyl
Pr=propyl
TFA=trifluoroacetic acid
THF=tetrahydrofuran
TLC or tlc=thin layer chromatography The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail.

The compounds and pharmaceutically acceptable salts of the present invention can be synthesized according to the general methods outlined in Schemes 1–5 and the description of the schemes and examples which follow.

The compounds of the present invention are prepared by a two step alkylation process beginning with a saccharin or substituted saccharin (referred to as "the saccharin moiety") prepared according to methods known in the art (see for example U.S. Pat. Nos. 4,818,756; 4,937,343; 4,988,809 and 5,187,276, hereby incorporated by reference for this purpose). The saccharin moiety is alkylated with a reagent such as 1,4-dibromobutane, or a similar reagent, to form the butyl-saccharin moiety (see Scheme 1 and Examples 21 and 22 below). The butyl saccharin is then alkylated with a piperidinyl benzoxazolinone (prepared as shown in Examples 17–19 which follow) or with a piperidinyl benzimidazolinone (prepared as shown in Schemes 1–4 below) to form the active compounds of this invention. Various $N^3$-substituted benzimidazolinone-piperidine derivatives are prepared by alkylating the Boc-protected benzimidazolinone-piperidine as shown in Scheme 1 and Example 1, steps 1–3 below). The benzimidazolinone-piperidine derivatives with substituents on the benzene ring are prepared as shown in Schemes 4 and 5 using procedures described in *J. Med. Chem.*, 30, 814–819 (1987) and U.S. Pat. No. 3,910,930, hereby incorporated by reference. Compounds wherein the alkyl chain between the saccharin moiety and the piperidine ring is branched (i.e., compounds of the present invention wherein $R^3$ is cycloalkyl or unsubstituted or substituted alkyl) can be prepared according to Schemes 2 and 3. These steps are further defined with reference to the following schemes and synthetic examples appended hereto. It should be understood that the specific solvents, catalysts and reactants could be substituted by analogous reagents by those skilled in the art. Unless otherwise indicated, all substituents are as defined above.

SCHEME 1

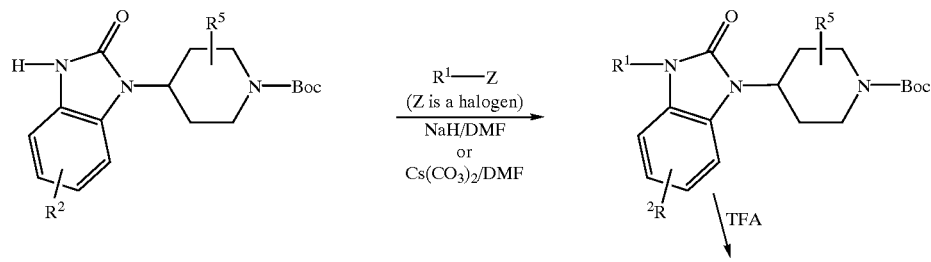

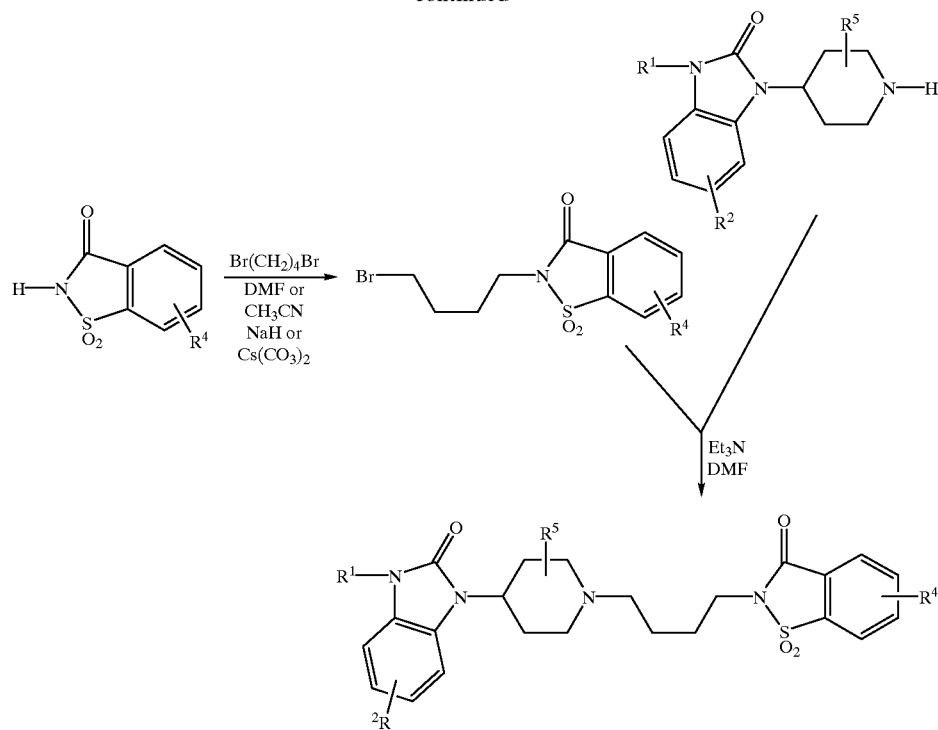
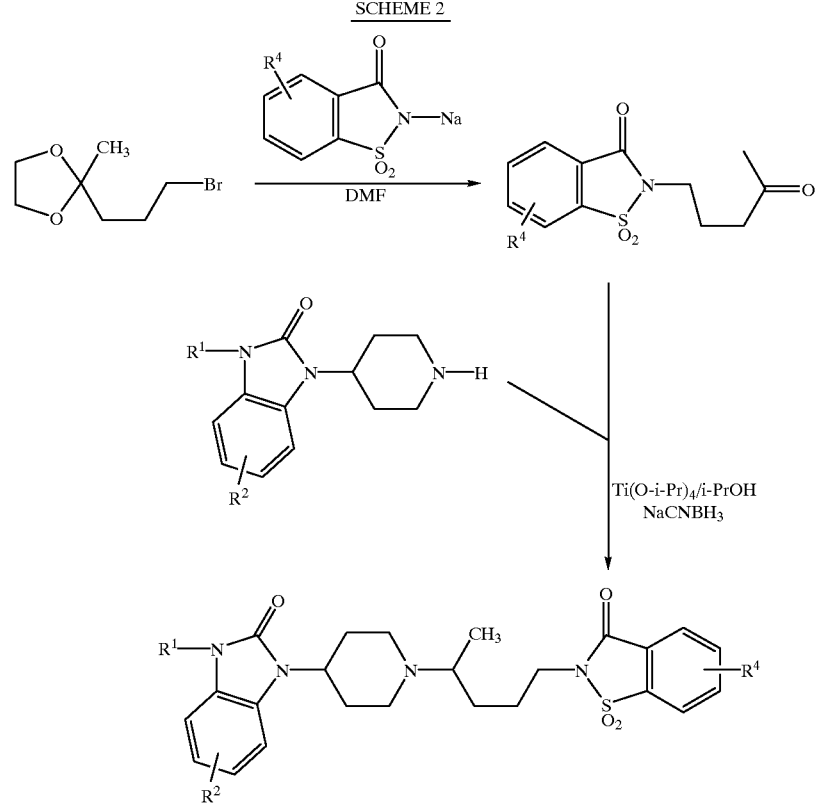
SCHEME 2

SCHEME 3
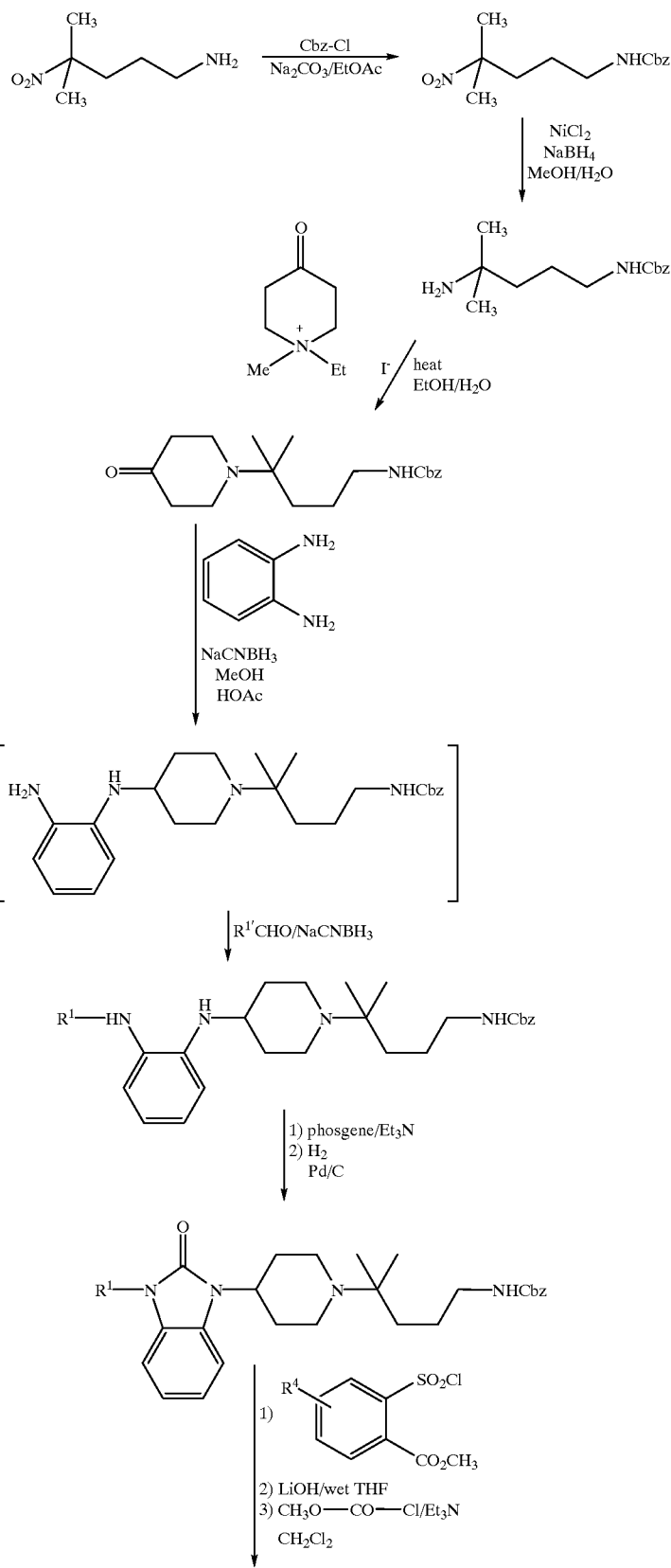

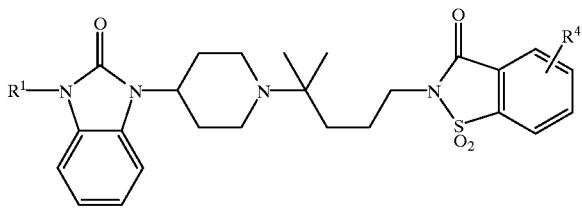
SCHEME 4
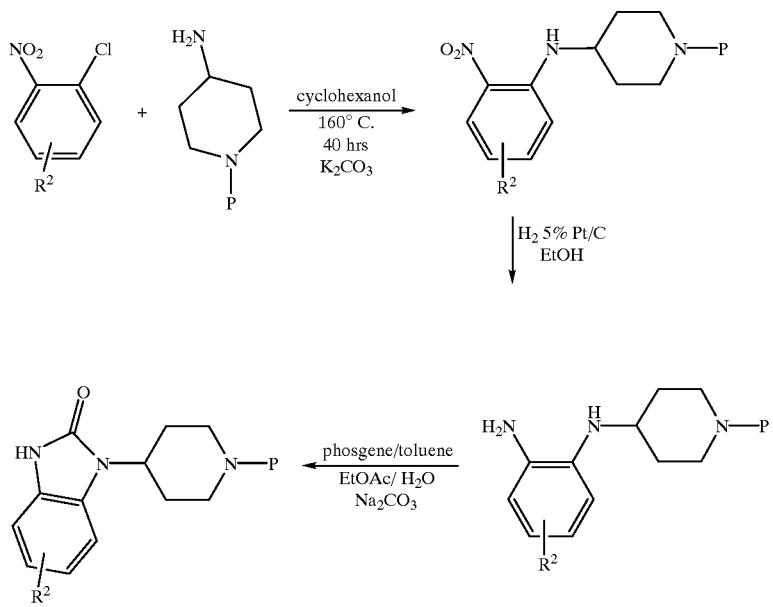
where P is a protecting group
Preferred compounds of the present invention, prepared according to the procedures described herein, are shown below in Table 1.
TABLE 1
| Compound | $R^1$ | $R^2$ | $R^4$ |
|---|---|---|---|
| A | $CF_3CH_2$ | F | Cl |
| B | $CF_3CH_2$ | $CH_3$ | Cl |
| C | $CF_3CH_2$ | Cl | Cl |
| D | $FCH_2CH_2$ | Cl | Cl |
| E | $CF_3CH_2$ | F | $OCH_2CH_3$ |
| F | $CF_3CH_2$ | F | H |
| G | $CF_3CH_2$ | F | $OCF_3$ |
| H | $FCH_2CH_2$ | F | Cl |
| J | $CF_3CH_2$ | Cl | H |
| K | $CH_3CH_2$ | Cl | Cl |

More specifically, Compound A is prepared according to Scheme 5 and the procedure of Example 27.
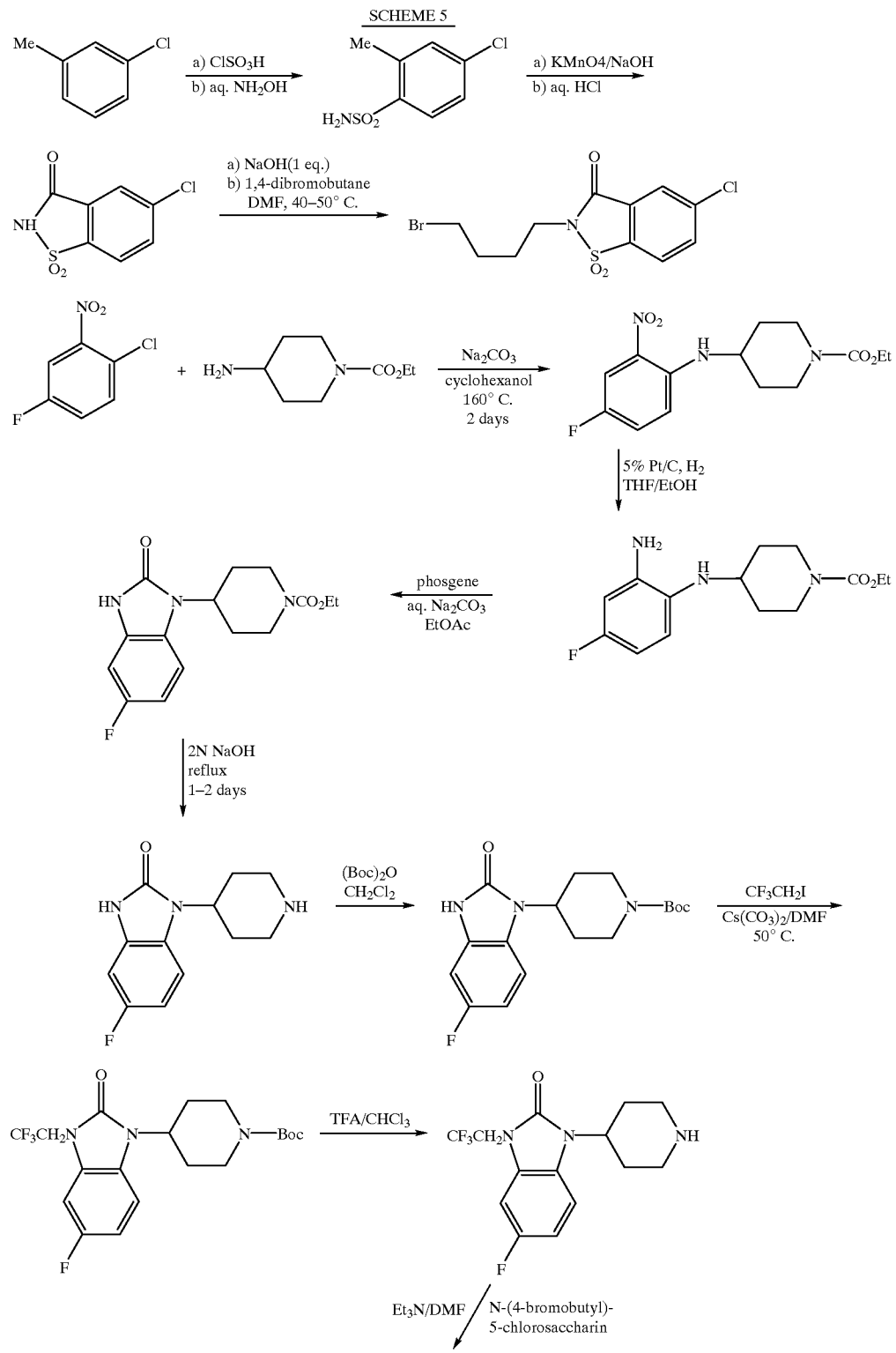

-continued

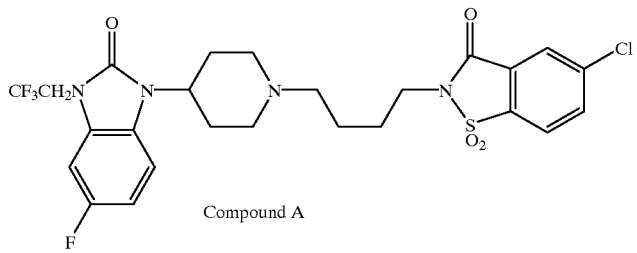

Compound A

The following examples are provided to further define the invention without, however, limiting the invention to the particulars of these examples.

EXAMPLE 1

1,1-Dioxido-2-(4-(4-(3-Propyl-2-oxo-1-benzimidazolinyl)piperidin-1-yl)butyl)-5-chloro-1,2-benzisothiazol-3-(2H)-one Step 1: To a partial suspension of 4-(2-oxo-1-benzimidazolinyl) piperidine (1.085 gm, 5.0 mmol), which is commercially available, in 30 mL of methylene chloride under an argon atmosphere was added 1.37 gm (6.3 mmol) of di-t-butyl dicarbonate. After reaction was stirred at ambient temp. for 1 hour, the solvent was removed and the residue triturated with diethyl ether to give 1-t-butoxycarbonyl-4-(2-oxo-1-benzimidazolinyl)piperidine as an off-white solid, melting point 161–163° C.

Step 2: To a solution of 1-t-butoxycarboxyl-4-(2-oxo-1-benzimidazolinyl)-piperidine (542 mg, 1.7 mmol) in dry dimethylformamide (5 mL) under an argon atmosphere was added 86 mg (2.0 mmol) of 60% sodium hydride in mineral oil. The mixture was warmed at 50° C. until gas evolution ceased (~½ hour) and then cooled to room temperature. Iodopropane (0.29 mL, 3.0 mmol) was added by syringe and the reaction was stirred for 20–48 hours. Water was added to the reaction mixture and the product extracted into ethyl acetate. After back-washing twice with water and then brine, the extract was evaporated to give 1-t-butoxycarbonyl-4-(3-propyl-2-oxo-1-benzimidazolinyl)piperidine as an oil which slowly crystallized, melting point 102–105° C.

Step 3: A solution of 1-t-butoxycarbonyl-4-(3-propyl-2-oxo-1-benzimidazolinyl)piperidine (540 mg, 1.5 mmol) in chloroform (7 mL) containing trifluoroacetic acid (1 mL) was allowed to stir at ambient temperature for 15–25 hours. The solvent was removed on a rotary evaporator, the residue dissolved in chloroform and washed with aq. $Na_2CO_3$. The dried ($Na_2SO_4$) chloroform extract was evaporated to give 4-(3-propyl-2-oxo-1-benzimidazolinyl)piperidine as an oil which was used as is.

Step 4: To a solution of 4-(3-propyl-2-oxo-1-benzimidazolinyl)piperidine (440 mg, 1.7 mmol) in dry dimethylformamide (6 mL), under an argon atmosphere was added 1,1-dioxido-2-(4-bromobutyl)-5-chloro-1,2-benzisothiazol-3(2H)-one (615 mg, 1.74 mmol, prepared as shown in Example 22) followed by triethylamine (0.25 mL, 1.8 mmol). This solution was heated at 50° C. for four hours and then cooled to room temperature as water was added. The product was extracted, dried ($Na_2SO_4$) and evaporated. The residue was chromatographed on a column of silica gel eluting with a gradient of 0.5–2% methanol/chloroform containing 0.2% $NH_4OH$ to give 1,1-dioxido-2-(4-(4-(3-propyl-2-oxo-1-benzimidazolinyl)piperidin-1-yl)butyl)-5-chloro-1,2-benzisothiazol-3(2H)-one as a viscous oil. $^1H$ NMR (400 MHz, $CDCl_3$): d 8.02 (s, 1H), 7.84 (quartet, J=8 Hz, 2H), 7.30 (broad d, 1H), 7.05 (broad quintet, 2H), 6.98 (broad d, J=8 Hz, 1H), 4.40 (multiplet, 1H), 3.84 (t, J=7.1 Hz, 4H), 3.07 (broad d, J=11.1 Hz, 2H),2.43–2.47 (m, 4H),2.14 (broad t, J=11 Hz, 2H), 1.88–1.93 (quintet, 2H), 1.75–1.81 (multiplet, 4H), 1.62–1.66 (multiplet, 2H), 0.97 (t, J=7.3 Hz, 3H). This oil was converted to its hydrochloride salt and crystallized from methanol upon addition of diethyl ether to give a crystalline white solid, melting point 225–227° C.: Analysis calculated for $C_{26}H_{31}ClN_4O_4S.HCl$: C, 55.02; H, 5.68; N, 9.87; found: C, 54.76; H, 5.66; N, 9.80.

EXAMPLE 2

(±) 1,1-Dioxido-2-(4-(4-(3-ethyl-2-oxo-1-benzimidazolinyl)piperidin-1-yl)pentyl)-1-2-benzisothiazol-3(2H)-one Step 1: A mixture of 12.8 gm (77 mmol) of 5-bromo-2-pentanone, which was obtained as described by ApSimon and Sequin in *Synthetic Communications,* 10, 897 (1980), and 12 mL of ethylene glycol in 100 mL of benzene containing 0.84 gm of p-toluenesulfonic acid was refluxed with a Dean-Stark trap until the required water was azeotroped off. The solution was poured into saturated $NaHCO_3$ and the product extracted into ethyl acetate. The dried ($Na_2SO_3$) solution was evaporated to give the ethylene ketal of 5-bromo-2-pentanone which was used as is.

Step 2: A mixture of the above ketal (3.2 gm, 15 mmol) and sodium saccharin (3.1 gm, 14 mmol) in dimethylformamide (15 mL) was heated at 170° C. for 5 hours. The cooled reaction mixture was poured into water and the crude product extracted into ethyl acetate. The dried extract was evaporated and the crude product was chromotographed on a column of silica gel eluting with a gradient of 20–40% EtOAc/hexane to give crystalline 1,1-dioxido-2-(4-oxo-pentyl)-1,2-benzisothiazol-3(2H)-one, melting point 90–93° C.

Step 3: A mixture of 4-(3-ethyl-2-oxo-1-benzimidazolinyl)piperidine (319 mg, 1.0 mmol) and 1,1-dioxido-2-(4-oxo-pentyl)-1,2-benzisothiazol-3-(2H)-one (267 mg, 1.0 mmol) in isopropanol (0.4 mL) containing titanium (IV) isoproproxide (0.4 mL, 1.3 mmol) was heated at 55° C. under an argon atmosphere for one hour to give a yellow solution. This solution was cooled to room temperature and diluted with absolute EtOH (4 mL). Sodium cyanoborohydride (70 mg, 1.1 mmol) was added and the reaction mixture stirred for 20 hours. Upon dilution of the reaction with water and addition of aq. $NaHCO_3$, the product was extracted into EtOAc, the extract dried ($Na_2SO_4$) and evaporated. The crude residue was chromotographed on a column of silica gel and eluted with a gradient of 0.25–1.25% methanol/chloroform to give (±)1,1-dioxido-2-(4-(4-(3-ethyl-2-oxo-1-benzimidazolinyl)piperidin-1-yl)pentyl)-1,2-benzisothiazol-3(2H)-one (referred to herein as Compound L) as a viscous oil. $^1$H NMR (400 mHz, $CDCl_3$): d 8.07 (dd, J=5.5 Hz, J=1.4 Hz, 1H), 7.93 (dd, J=6.5 Hz, J=1.1 Hz, 1H), 7.85 (quintet, 2H), 7.35–7.37 (m, 1H), 7.05 (quintet, 2H), 6.98–7.02 (m, 1H), 4.33–4.38 (m, 1H), 3.93 (q, J=7.1 Hz, 2H), 3.85 (dt, J=7.3 Hz, J=3.6 Hz, 2H), 2.86–2.90 (m, 2H), 2.73 (quartet, J=6.8, 1H), 2.57 (broad t, J=10 Hz, 1H), 2.26–2.49 (overlapping quintets, 3H), 1.97 (quintet, 2H), 1.80 (broad d, J=10 Hz, 2H), 1.61–1.69 (m, 1H), 1.41–1.48 (m, 1H), 1.33 (t, J=7.1 Hz, 3H), 1.00 (d, J=6.6 Hz, 3H). The residual oil was converted to its hydrochloride salt and crystallized from isopropanol to give a white crystalline solid, melting point 176° C. (Compound L). Analysis calculated for $C_{26}H_{32}N_4O_4S \cdot HCl \cdot 0.3H_2O$: C, 57.99; H, 6.29; N, 10.41; found: C, 58.03; H, 6.19; N, 10.38.

Step 4: Compound L was chromatographed on a chiral HPLC column (Chiralcel OD®, Chiral Technologies Inc., Exton, Pa.) eluting under isocratic conditions with a 90%hexane/10% 1-butanol/0.1% diethylamine solvent mixture to afford the two enantiomers, designated as Enantiomer 1 and Enantiomer 2.

EXAMPLE 3

1,1-Dioxido-2-(4-(4-(3-Ethyl-2-oxo-1-benzimidazolinyl)piperidin-1-yl)4-methylpentyl)-1,2-benzisothiazol-3(2H)-one Step 1: A solution of 5-(benzyloxycarbonylamino)-2-methyl-2-pentylamine (1.59 gm, 6.3 mmol) [prepared as described by Nagarajan and Ganem, *J. Org. Chem.*, 51, 4856 (1986) except that a benzyloxycarbonyl protecting group was used in place of a t-butoxycarbonyl group] in ethanol (14 mL) containing potassium carbonate (101 mg, 0.7 mmol) was heated at 80° C. and a solution of methyl ethylpiperidonium iodide (2.54 gm, 9.45 mmol) [obtained by a dropwise addition of one equivalent of methyl iodide to n-ethyl-4-piperidone in acetone] in water (45 mL) was added dropwise over a 2 hour period. After heating the reaction mixture for 4 more hours, the reaction was cooled, diluted with water and aq. $Na_2CO_3$ and the crude product extracted into chloroform. This extract was dried ($Na_2SO_4$) and the solvent evaporated. The residue was chromatographed on a column of silica gel eluting with a gradient of 0.5–3% methanol/chloroform containing 0.2% $NH_4OH$ to give N-(5-benzyloxycarbonylamino-2-methyl-2-pentyl)-4-piperidone as an oil.

Step 2: An equivalent of phenylene diamine (118 mg, 1.09 mmol) was added to a solution of N-(5-benzyloxycarbonylamino-2-methyl-2-pentyl)4-piperidone (345 mg, 1.04 mmol) in methanol (5 mL) containing acetic acid (0.065 mL, 1.15 mmol). After stirring this reaction mixture for one hour, solid sodium cyanoborohydride (82 mg, 1.3 mmol) was added in one portion and stirring was continued overnight at ambient temperature. The reaction was cooled in an ice bath and acetaldehyde (0.06 mL, 1.0 mmol) was added by syringe. The reaction was stirred for an additional 20 hours. Water and aq. $Na_2CO_3$ was then added to the reaction mixture and the crude product extracted into chloroform. The dried ($Na_2SO_4$) chloroform extract was filtered through a pad of charcoal and the solvent evaporated to give a 1:1 mixture of 1-(5-benzyloxycarbonylamino-2-methyl-2-pentyl)-4-(2-ethylamino anilino)piperidine and by-product 1-(5-benzyloxycarbonylamino-2-methyl-2-pentyl)-4-(2-diethylaminoanilino)piperidine. This mixture was used as is in the next step.

Step 3: The above mixture was dissolved in ethyl acetate (8 mL), saturated aq. $Na_2O_3$ (6 mL) was added, and the biphase mixture cooled in an ice bath as 1.9M phosgene/toluene (1 mL) was added dropwise. After 4–20 hours, the reaction mixture was diluted with water and the crude product extracted into ethyl acetate. The dried ($Na_2SO_4$) ethyl acetate solution was evaporated and the residue chromatographed on a column of silica gel eluting with a gradient of 0.25–3% methanol/chloroform containing 0.2% $NH_4OH$ to give 1-(5-benzyloxycarbonylamino-2-methyl-2-pentyl)-4-(3-ethyl-2-oxo-1-benzimidazolinyl)piperidine as a viscous oil.

Step 4: A solution of 1-(5-benzyloxycarbonylamino-2-methyl-2-pentyl)-4-(3-ethyl-2-oxo-1-benzimidazolinyl) piperidine (93 mg, 0.19 mmol) in methanol (8 mL) containing chloroform (0.04 mL, 0.05 mmol) and 10% palladium/carbon (45 mg) was hydrogenated at atmospheric pressure for two days. The catalyst was removed by filtration, the solvent evaporated and the residue redissolved in chloroform. This solution was washed with aq. $Na_2CO_3$, dried ($Na_2SO_4$) and evaporated to give 1-(5-amino-2-methyl-2-pentyl)-4-(3-ethyl-2-oxo-1-benzimidazolinyl)piperidine as an oil.

Step 5: A solution of 1-(5-amino-2-methyl-2-pentyl)-4-(3-ethyl-2-oxo-1-benzimidazolinyl)piperidine (67 mg, 0.19 mmol) in methylene chloride (4 mL) was cooled in an ice bath and methyl 2-chlorosulfonyl benzoate (5.5 mg, 0.25 mmol) and triethylamine (0.04 mL, 0.3 mmol) were added. After one hour aq. $Na_2CO_3$ was added to the reaction mixture and the product extracted into methylene chloride, dried ($Na_2SO_4$) and evaporated. This residue was dissolved in wet tetrahydrofuran (4 mL) and lithium hydroxide hydrate (20 mg, 0.47 mmol) was added. After stirring this reaction mixture overnight, the pale yellow solution was evaporated. The residue was dissolved in methylene chloride (4 mL) and triethyl amine (0.07 mL, 0.5 mmol) added, followed by excess methyl chloroformate (0.12 mL). After one hour, aq $Na_2CO_3/NaHCO_3$ was added and the methylene chloride extract dried ($Na_2SO_4$) and evaporated. This residue was chromatographed on a silica gel column eluting with a gradient of 0.5–2% methanol/chloroform containing 0.2% $NH_4OH$ to give 1,1-dioxido-2-(4-(4-(3-ethyl-2-oxo-1-benzimidazolinyl)piperidin-1-yl)4-methyl pentyl)-1,2-benzisothiazol-3(2H)-one as a viscous oil. $^1$H NMR (400 mHz, $CDCl_3$): d 8.06 (dd, J=6.8 Hz, J=1.2 Hz, 1H), 7.92 (dd, J=7 Hz, J=1.6 Hz, 1H), 7.80–7.89 (quintet, 2H), 7.30–7.33 (m, 1H), 7.03–7.07 (m, 2H), 6.98–7.01 (m, 1H), 4.31–4.37 (m, 1H), 3.93 (quartet, J=7.2 Hz, 2H), 3.82 (t, J=7.3 Hz, 2H), 3.08 (broad d, J=10.3 Hz, 2H), 2.22–2.38 (overlapping quintets, 4H), 1.94–2.02 (quintet, 2H), 1.79 (broad d, J=10.9 Hz, 2H), 1.53–1.57 (multiplet, 2H), 1.33 (t, J=7.3 Hz, 3H), 1.06 (s, 6H).

This viscous oil was converted to its hydrochloride salt and crystallized from acetonitrile by addition of diethyl ether to give a crystalline white solid, melting point 182–185° C.: analysis calculated for $C_{27}H_{34}N_4O_4S.HCl.0.4\ H_2O$: C, 58.51; H, 6.51; N, 10.11; found: C, 58.51; H, 6.38; N, 10.04.

EXAMPLE 4

1,1-Dioxido-2-(4-(4-(3-ethyl-2-oxo-1-benzimidazolinyl)piperidin-1-yl)butyl)-1,2-benzisothiazol-3(2H)-one From 4-(3-ethyl-2-oxo-1-benzimidazolinyl)piperidine and 1,1-dioxido-2-(4-bromobutyl)-1,2-benzisothiazol-3 (2H)-one (prepared as shown in Example 21) using the procedures described in Example 1 there was obtained a white solid as the freebase (from diethyl ether), melting point 124–25° C. Analysis calculated for $C_{25}H_{30}N_4O_4S.0.4\ H_2O$: C, 61.30; H, 6.34; N, 11.44; found: C, 61.34; H, 6.18; N, 11.47. The NMR was consistent with the structure.

EXAMPLE 5

1,1-Dioxido-2-(4-(4-(3-(2,2,2-trifluoroethyl)-2-oxo-1-benzimidazolinyl)piperidin-1-yl)butyl)-1,2-benzisothiazol-3(2H)-one From 4-(3-(2,2,2-trifluoroethyl)-2-oxo-1-benzimidazolinyl)piperidine [prepared by a modification of Step 2 of Example 1 wherein cesium carbonate replaced the sodium hydride and the reaction was heated at 50° C. for 20 hours] and 1,1-dioxido-2-(4-bromobutyl)-1,2-benzisothiazol-3(2H)-one (prepared as shown in Example 21) using the procedures described in Example 1 there was obtained a white solid upon formation of the HCl salt (from isopropanol and diethyl ether), melting point 231–234° C. Analysis calculated for $C_{25}H_{27}F_3N_4O_4S.HCl$: C, 52.40; H, 4.92; N, 9.78; found: C, 52.02; H, 4.86; N, 9.62. The NMR was consistent with the structure.

EXAMPLE 6

1,1-Dioxido-2-(4-(4-(3-n-propyl-2-oxo-1-benzimidazolinyl)piperidin-1-yl)butyl)-1,2-benzisothiazol-3(2H)-one From 4-(3-n-propyl-2-oxo-1-benzimidazolinyl)piperidine and 1,1-dioxido-2-(4-bromobutyl)-1,2-benzisothiazol-3 (2H)-one (prepared as shown in Example 21) using the procedures described in Example 1 there was obtained a white solid upon formation of the HCl salt (from isopropanol and diethyl ether), melting point 214–216° C. Analysis calculated for $C_{26}H_{32}N_4O_4S.HCl$: C, 58.58; H, 6.24; N, 10.51; found: C, 58.43; H, 6.22; N, 10.50. The NMR was consistent with the structure.

EXAMPLE 7

1,1-Dioxido-2-(4-(4-(3-benzyl-2-oxo-1-benzimidazolinyl)piperidin-1-yl)butyl)-1,2-benzisothiazol-3(2H)-one From 4-(3-benzyl-2-oxo-1-benzimidazolinyl)piperidine and 1,1-dioxido-2-(4-bromobutyl)-1,2-benzisothiazol-3 (2H)-one (prepared as shown in Example 21) using the procedures described in Example 1 there was obtained a white solid upon formation of the HCl salt (from isopropanol), melting point 212–214° C. Analysis calculated for $C_{30}H_{32}N_4O_4S.HCl.0.4\ H_2O$: C, 61.33; H, 5.78; N, 9.54; found: C, 61.29; H, 5.64; N, 9.52. The NMR was consistent with the structure.

EXAMPLE 8

1,1-Dioxido-2-(4-(4-(3-ethyl-2-oxo-1-benzimidazolinyl)piperidin-1-yl)butyl-5-chloro-1,2-benzisothiazol-3(2H)-one From 4-(3-ethyl-2-oxo-1-benzimidazolinyl)piperidine and 1,1-dioxido-2-(4-bromobutyl)-5-chloro-1,2-benzisothiazol-3(2H)-one (prepared as shown in Example 22) using the procedures described in Example 1 there was obtained a white solid upon formation of the HCl salt (from methanol), melting point 246–248° C. Analysis calculated for $C_{25}H_{29}ClN_4O_4S.HCl.0.45\ H_2O$: C, 53.46; H, 5.55; N, 9.98; found: C, 53.44; H, 5.38; N, 9.88. The NMR was consistent with the structure.

EXAMPLE 9

1,1-Dioxido-2-(4-(4-(3-(2-fluoroethyl)-2-oxo-1-benzimidazolinyl)piperidin-1-yl)butyl-5-chloro-1,2-benzisothiazol-3(2H)-one From 4-(3-(2-fluoroethyl)-2-oxo-1-benzimidazolinyl) piperidine and 1,1-dioxido-2-(4-bromobutyl)-5-chloro-1,2-benzisothiazol-3(2H)-one (prepared as shown in Example 22) using the modified procedures described in Example 5 there was obtained a white solid upon formation of the HCl salt (from methanol), melting point 246–248° C. Analysis calculated for $C_{25}H_{28}ClFN_4O_4S.HCl$: C, 52.54; H, 5.11; N, 9.80; found: C, 52.53; H, 5.11; N, 9.73. The NMR was consistent with the structure.

EXAMPLE 10

1,1-Dioxido-2-(4-(4-(3-ethyl-2-oxo-1-benzimidazolinyl)piperidin-1-yl)butyl)-4,5-ethylenedioxy-1,2-benzisothiazol-3(2H)-one From 4-(3-ethyl-2-oxo-1-benzimidazolinyl)piperidine and 1,1-dioxido-2-(4-bromobutyl)-4,5-ethylenedioxy-1,2-benzisothiazol-3(2H)-one (prepared as shown in Example 25) using the procedures described in Example 1 there was obtained a white solid upon formation of the HCl salt (from isopropanol), melting point 215–217° C. Analysis calculated for $C_{27}H_{32}N_4O_6S.HCl.0.75$ isopropanol.$0.15\ H_2O$: C, 56.22; H, 6.34; N, 8.97; found: C, 56.22; H, 6.35; N, 8.94. The NMR was consistent with the structure.

EXAMPLE 11

1,1-Dioxido-2-(4-(4-(5-methyl-3-ethyl-2-oxo-1-benzimidazolinyl)piperidin-1-yl)butyl)-5-chloro-1,2-benzisothiazol-3(2H)-one From 4-(5-methyl-3-ethyl-2-oxo-1-benzimidazolinyl) piperidine and 1,1-dioxido-2-(4-bromobutyl)-5-chloro-1,2-benzisothiazol-3(2H)-one (prepared as shown in Example 22) using the procedures described in Example 1 there was obtained a white solid upon formation of the HCl salt (from methanol), melting point 229–231° C. Analysis calculated for $C_{26}H_{31}N_4O_4S \cdot HCl \cdot 0.75\ H_2O$: C, 53.82; H, 5.80; N, 9.66; found: C, 53.79; H, 5.52; N, 9.53. The NMR was consistent with the structure.

EXAMPLE 12

1,1-Dioxido-2-(4-(4-(2-oxo-1-benzimidazolinyl) piperidin-1-yl)-4-methylpentyl)-1,2-benzisothiazol-3 (2H)-one Using the procedures described in Example 3, except that in Step 2, the addition of acetaldehyde was omitted, there was obtained a white solid upon formation of the HCl salt (from methanol), melting point 176° C. Analysis calculated for $C_{25}H_{30}N_4O_4S \cdot HCl \cdot 0.2\ H_2O$: C, 57.45; H, 6.06; N, 10.72; found: C, 57.42; H, 5.98; N, 10.66. The NMR was consistent with the structure.

EXAMPLE 13

1,1-Dioxido-2-(4-(4-(2-oxo-1-benzimidazolinyl) piperidin-1-yl)pentyl)-1,2-benzisothiazol-3(2H)-one From 4-(2-oxo-1-benzimidazolinyl)piperidine and 1,1-dioxido-2-(4-oxo-pentyl)-1,2-benzisothiazol-3(2H)-one using the procedures of Example 2 there was obtained a white solid upon formation of the HCl salt (from isopropanol), melting point 223–225° C. Analysis calculated for $C_{24}H_{28}N_4O_4S \cdot HCl \cdot 0.9$ isopropanol: C, 57.35; H, 6.53; N, 10.02; found: C, 57.09; H, 6.36, N, 10.00. The NMR was consistent with the structure.

EXAMPLE 14

1,1-Dioxido-2-(4-(4-(3-isopropyl-2-oxo-1-benzimidazolinyl)piperidin-1-yl)butyl)-5-chloro-1,2-benzisothiazol-3(2H)-one From 4-(3-isopropyl-2-oxo-1-benzimidazolinyl) piperidine and 1,1-dioxido-2-(4-bromobutyl)-5-chloro-1,2-benzisothiazol-3(2H)-one (prepared as shown in Example 22) using the procedures described in Example 1 there was obtained a white solid upon formation of the HCl salt (from methanol and diethyl ether), melting point 229–234° C. Analysis calculated for $C_{26}H_{31}ClN_4O_4S \cdot HCl \cdot 0.4\ H_2O$: C, 54.33; H, 5.75; N; 9.75; found: C, 54.35; H, 5.60; N, 9.70. The NMR was consistent with the structure.

EXAMPLE 15

1,1-Dioxido-2-(4-(4-(3-butyl-2-oxo-1-benzimidazolinyl)piperidin-1-yl)butyl)-5-chloro-1,2-benzisothiazol-3(2H)-one From 4-(3-butyl-2-oxo-1-benzinidazolinyl)piperidine and 1,1-dioxido-2-(4-bromobutyl)-5-chloro-1,2-benzisothiazol-3(2H)-one using the procedures described in Example 1 there was obtained a white solid upon formation of the HCl salt (from methanol), melting point 192–195° C. Analysis calculated for $C_{27}H_{334}N_4O_4S \cdot HCl \cdot 0.8\ H2O$: C,54.41; H,6.02; N,9.40; found: C,54.41; H,5.82; N,9.34. The NMR was consistent with the structure.

EXAMPLE 16

1,1-Dioxido-2-(4-(4-(3-(2,2,2-trifluoroethyl)-2-oxo-1-benzimidazolinyl)piperidin-1-yl)butyl)-5-chloro-1, 2-benzisothiazol-3(2H_1-one From 4-(3-(2,2,2-trifluoroethyl)-2-oxo-1-benzimidazolinyl)piperidine [prepared by a modification of Step 2 of Example 1 wherein cesium carbonate replaced the sodium hydride and the reaction was heated at 50° C. for 20 hours] and 1,1-dioxido-2-(4-bromobutyl)-5-chloro-1,2-benzisothiazol-3(2H)-one using the procedures described in Example 1 there was obtained a white solid upon formation of the HCl salt (from methanol and diethyl ether), melting point 237–239° C. Analysis calculated for $C_{25}H_{26}ClF_3N_4O_4S \cdot HCl \cdot 0.4\ H2O$: C,48.85; H,4.56; N,9.12; found: C,48.83 ; H,4.53 ; N,9.04. The NMR was consistent with the structure.

EXAMPLE 17

(±) 1,1-Dioxido-2-(4-(4-(2-oxo-3-benzoxazolinyl) piperidin-1-yl)pentyl)-1,2-benzisothiazol-3(2H)-one Step 1: A mixture of 15.4 g 4-piperidone hydrochloride hydrate, 200 mL ether, 100 mL saturated aqueous $Na_2CO_3$ solution and 21.8 g di-t-butyldicarbonate was vigorously stirred for 48 h. The layers were separated and the organic layer was washed with two 150 mL portions of 10% aqueous citric acid, dried over $MgSO_4$. Removal of solvents under reduced pressure gave N-t-butyloxycarbonyl-4-piperidone as a white solid.

Step 2: A mixture of 6.0 g N-t-butyloxycarbonyl-4-piperidone, 3.3 g of 2-aminophenol, 25 mL of 1,2-dichloroethane, 25 mL of glacial acetic acid, and 500 mg powdered 4 Å molecular sieves was stirred under inert atmosphere. After 30 min, 6.4 g sodium triacetoxyborohydride was added stirring was continued for 38 h. The reaction mixture was poured into 400 mL ethyl acetate and 200 mL saturated aqueous $NaHCO_3$ and the layers separated. The organic layer was washed with brine (2×100 mL), dried over $MgSO_4$, filtered and concentrated under reduced pressure. Chromatography of the crude product on silica gel, eluting with a gradient of 1–3% methanol/methylene chloride containing 0.5% concentrated $NH_4OH$ gave 1-t-butyloxycarbonyl-4-(2-hydroxyphenylamino)piperidine as an orange foam.

Step 3: To a stirred solution of 6.95 g 1-t-butyloxycarbonyl-4-(2-hydroxyphenylamino)piperidine and 6.2 mL diisopropylethylamine in 120 mL tetrahydrofuran cooled to 0° C. was added 3.0 g triphosgene. The reaction was stirred 30 min at 0° C. and then at room temperature 2 h. The precipitate was removed by filtration, the filtrate concentrated at reduced pressure and partitioned between 250 mL ethyl acetate and 100 mL saturated aqueous $Na_2CO_3$. The layers were separated, the organic layer washed with 100 mL of saturated aqueous $Na_2CO_3$, 100 mL of water, 100 mL of brine, dried over $MgSO_4$, and concentrated under reduced pressure. Chromatography of the crude product on silica gel, eluting with a gradient of 40–50% ethyl acetate-hexanes gave 1-((1-t-butyloxycarbonyl) piperidin-4-yl)-3-benzoxazolin-2-one as a yellow foam.

Step 4: A stirred solution of 6.0 g (19 mmol) 1-((1-t-butyloxycarbonyl)piperidin-4-yl)-3-benzoxazolin-2-one in 120 mL ethyl acetate was cooled to −78° C. and a stream of hydrogen chloride gas was introduced with a fritted dispersion tube for 15 min. The mixture was allowed to warm to 0° C. for 1 h, ten room temperature for 2 h. The resulting precipitate was collected by filtration. Drying at reduced pressure for 8 h gave the hydrochloride salt of 1-(4-piperidinyl)-3-benzoxazolin-2-one as an off-white solid.

Step 5: From 1-(4-piperidinyl)-3-benzoxazolin-2-one and 1,1-dioxido-2-(4-oxo-pentyl)-1,2-benzisothiazol-3(2H)-one using the procedures of Example 2 there was obtained a white solid upon formation of the HCl salt (from isopropanol and methanol), melting point 273–274° C. Analysis calculated for $C_{24}H_{27}N_3O_5S.HCl$ : C, 56.96; H, 5.58; N, 8.30; found: C, 56.59; H, 5.67, N, 8.01. The NMR was consistent with the structure.

EXAMPLE 18

(±)1,1-Dioxido-2-(4-(4-(6-methyl-2-oxo-3-benzoxazolinyl)piperidin-1-yl)pentyl)-1,2-benzisothiazol-3(2H)-one Step 1: 4-(6-methyl-2-oxo-3-benzoxazolinyl)piperidine was obtained as a white solid from the reaction of 6-amino-m-cresol and N-t-butyloxycarbonyl-4-piperidone according to Steps 2–4 of Example 17.

Step 2: From 4-(6-methyl-2-oxo-3-benzoxazolinyl) piperidine and 1,1-dioxido-2-(4-oxo-pentyl)-1,2-benzisothiazol-3(2H)-one using the procedures of Example 2 there was obtained a white solid upon formation of the HCl salt (from ethanol and diethyl ether), melting point 234–236° C. Analysis calculated for $C_{25}H_{29}N_3O_5S.HCl.0.4$ H2O: C, 56.95; H, 5.89; N, 7.97; found: C, 56.92; H, 5.75, N, 7.79. The NMR was consistent with the structure.

EXAMPLE 19

(±) cis/trans-1,1-Dioxido-2-(4-(4-(2-oxo-3-benzoxazolinyl)-2-methylpiperidin-1-yl)butyl)-1,2-benzisothiazol-3(2H)-one From (±)cis/trans-4-(2-oxo-1-benzoxazolinyl)-2-methylpiperidine (obtained from (±)2-methyl-4-piperidone utilizing methodology described in *J. Org. Chem.*, 55, 2578 (1990)) and 1,1-dioxido-2-(4-bromobutyl)-1,2-benzisothiazol-3(2H)-one (prepared as shown in Example 21) using the procedures described in Example 1 there was obtained a white solid upon formation of the HCl salt (from methanol and diethyl ether), melting point 216–224° C. Analysis calculated for $C_{24}H_{27}N_3O_5S.HCl.0.2$ ethanol.0.2 H2O: C, 54.48; H, 5.75; N, 8.10; found: C, 54.48; H, 5.68; N, 8.02. The NMR was consistent with the structure.

EXAMPLE 20

(±) cis/trans-1,1-Dioxido-2-(4-(4-(2-oxo-1-benzimidazolinyl)-3-methoxycarbonyl-piperidin-1-yl)butyl)-5-chloro-1,2-benzisothiazol-3(2H)-one Step 1: From phenylene diamine and methyl N-t-butoxycarbonyl-4-oxo-3-piperidinecarboxylate ( obtained by reaction of methyl 4-oxo-3-piperidinecarboxylate with di-t-butyl dicarbonate as described in Example 1, Step1) using the procedures described in Example 3, Step 2 (except that the acetaldehyde was omitted) and Step 3, followed by removal of the t-butoxycarbonyl group with HCl gas in ethyl acetate there was obtained (±) cis/trans-4-(2-oxo-1-benzimidazolinyl)-3-methoxycarbonyl-piperidine which was used as is.

Step 2: From (±) cis/trans-4-(2-oxo-1-benzimidazolinyl)-3-methoxycarbonyl-piperidine and 1,1-dioxido-2-(4-bromobutyl)-5-chloro-1,2-benzisothiazol-3(2H)-one (prepared as shown in Example 22) using the procedures described in Example 1, Step 3, there was obtained a white solid from methylene chloride, melting point 170–176° C. Analysis calculated for $C_{25}H_{27}ClN_4O_6S$: C, 54.89; H, 4.98; N, 10.24; found: C, 54.65; H, 4.98; N, 10.22. The NMR was consistent with the structure.

EXAMPLE 21

1,1-Dioxido-2-(4-bromobutyl)-1,2-benzisothiazol-3(2H)-one

The general procedure of J. D. Commerford and H. B. Donahue *J. Org. Chem.* 1956, 21, 583–4 was modified: A mixture of 6 g of sodium saccharin, 100 mL of 1,4-dibromobutane, and 5 mL of N,N-dimethylformamide was heated at 50° C. overnight. After cooling to ambient temperature, the mixture was diluted with 250 mL of ether and 50 mL of water. The aqueous layer was extracted with two additional 50 mL portions of ether and the combined organic extracts were dried over $MgSO_4$ and concentrated under reduced pressure. The excess 1,4-dibromobutane was removed by short path vacuum distillation and the oily residue purified by crystallization from ether-hexane, mp 71–2° C.

EXAMPLE 22

1,1-Dioxido-2-(4-bromobutyl)-5-chloro-1.2-benzisothiazol-3(2H)-one

The general procedure of J. D. Commerford and H. B. Donahue *J. Org. Chem.* 1956, 21, 583–4 was modified: A mixture of 0.5 g of 5-chloro-1,2-benzothiazol-3(2H)-one prepared as described by J. G. Lombardino, *J. Org. Chem.* 1971, 36, 1843–5, 1 mL of N,N-dimetbylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 mL of ethyl acetate, washed with 25 mL of sat'd $NaHCO_3$, 25 mL of sat'd brine and dried over $MgSO_4$. Removal of solvents under reduced pressure and vacuum distillation gave a crude product as a viscous oil which was free of 1,4-dibromobutane by $^1H$-NMR and was used without further purification.

EXAMPLE 23

1,1-Dioxido-2-(4-(4-(5-fluoro-3-ethyl-2-oxo-1-benzimidazolinyl)piperidin-1-yl)butyl)-5-chloro-1.2-benzisothiazol-3(2H)-one Starting with 4-(5-fluoro-3-ethyl-2-oxo-1-benzimidazolinyl)piperidine and 1,1-dioxido-2-(4-bromobutyl)-5-chloro-1,2-benzisothiazol-3(2H)-one and following the procedure of Example 1, the title compound was obtained as the HCl salt, melting point 266–268° C. The NMR was consistent with the structure.

EXAMPLE 24

(±) cis/trans-1,1-Dioxido-2-(4-(2-cyano-4-(3-propyl-2-oxo-1-benzimidazolinyl)piperidin-1-yl)butyl)-5-chloro-1.2-benzisothiazol-3(2H)-one Step 1: To a cloudy solution of 4-(3-n-propyl-2-oxo-1-benzimidazolinyl)- piperidine (420 mg, 1.62 mmol)

[obtained in Example 1, step 3] in diethyl ether (4.mL) which was cooled in an ice bath was added t-butyl hypochlorite (0.53 mL, 4.4 mmol) in three portions by syringe over a two hour period. When the starting amine had disappeared by tlc, the diluted etheral mixture was washed with water and the organic solution dried ($Na_2SO_4$). After concentration to about 4 mL, this etheral solution was added to a suspension of potassium superoxide (253 mg, 3.56 mmol) in diethyl ether (10 mL) containing 18-crown-6 ether (10 mg) and stirred vigorously for 15–20 hours. This mixture was filtered and the etheral filtrate was added dropwise to a solution of tri-methylsilyl cyanide (0.50 mL, 3.56 mmol) in diethyl ether (5 mL) cooled in an ice bath. After one hour the solution was washed with water and brine and then dried ($Na_2SO_4$) and evaporated. The residue was chromatograghed on a column of silica gel and eluted with 3% methanol/methylene chloride to give purified (±) cis/trans-2-cyano-4-(3-n-propyl-2-oxo-1-benzimidazolinyl) piperidine as a waxy solid which was used as is.

Step 2: From (±) cis/trans-2-cyano-4-(3-n-propyl-2-oxo-1-benzimidazolinyl)-piperidine and 1,1-dioxido-2-(4-bromobutyl)-5-chloro-1,2-benzisothiazol-3(2H)-one using a modification of the procedure described in Example 1, Step 4, wherein one equivalent of potassium iodide was added and the reaction was warmed at 80° C. for 24 hours, there was obtained a white solid after chromatographic purification, melting point 159–160° C. The NMR was consistent with structure.

EXAMPLE 25

1,1-Dioxido-2-(4-bromobutyl)-4,5-ethylenedioxy-1,2-benzisothiazol-3(2H)-one

Step 1: Chlorosulfonic acid (6 mL, 90 mmol) was added dropwise to an ice cooled solution of 1,4-benzodioxane (12 gm, 88 mmol) in chloroform (40 mL). After allowing the reaction mixture to warm to 20° C. (about 15 min.), this solution was poured on to ice (400 gm) and the product extracted into chloroform. This extract was dried ($MgSO_4$) and the solvent evaporated to give the 6-chlorosulfonyl-1,4-benzodioxane as a white crystalline solid. This sulfonyl chloride was dissolved in methylene chloride (100 mL) and added to an ice cooled solution of 4-amino-1-butanol (10 gm, 112 mmol) and excess triethylamine (25 mL) in methylene chloride (250 mL). After stirring for 24 hours and gradually warming to ambient temp., the reaction mixture was washed with 6N HCl (100 mL), dried ($MgSO_4$) and filtered. To this resulting solution was added 3,4-dihydro-2H-pyran (20 mL, 219 mmol) and p-toluenesulfonic acid (100 mg) and additional methylene chloride to bring the volume to 300 mL. After stirring at ambient temp. for 15–20 hours, the solution was washed with saturated aq. $Na_2CO_3$ (100 mL), dried ($MgSO_4$) and the solvent evaporated. The oily residue was chromatographed on a column of silica gel and eluted with 30% ethyl acetate/hexane to give the purified product as a colorless oil.

This azeotropically dried (from toluene) tetrahydropyranyl ether was dissolved in tetrahydrofuran (250 mL) under a nitrogen atmosphere and the solution cooled to –78° C. After the dropwise addition of 1.6 M n-butyl lithium/hexane (80 mmol), the reaction mixture was allowed to warm to 0° C. for two hours and then recooled to –78° C. as carbon dioxide gas was dispersed through the reaction mixture while maintaining the internal temp. below –50° C. for 30 min. The reaction was then allowed to warm to room temp. and the mixture was diluted with saturated aq. $Na_2CO_3$ (200 mL) and water (200 mL). The separated THF layer was washed with diluted $Na_2CO_3$ (2×100 mL). The combined $Na_2CO_3$ extracts were carefully acidified with conc. HCl and the product was extracted into diethyl ether (3×200 mL). The ether extracts were dried ($MgSO_4$) and the solvent evaporated to give the carboxylic acid as a glassy foam. This material was dissolved in methylene chloride (200 mL), cooled to 0° C., and triethylamine (7 mL) added followed by the dropwise addition of methyl chloroformate (2 mL). After stirring this reaction at room temp. for two hours, the solution was washed with saturated $Na_2CO_3$ (50 mL), dried ($MgSO_4$) and the solvent evaporated. The residue was dissolved in methanol (200 mL) containing p-toluenesulfonic acid hydrate (1 gm) and the reaction mixture stirred at ambient temp. for 20–24 hours. The methanol was removed by evaporation and the residue dissolved in ethyl acetate (200 mL). This solution was washed with saturated $Na_2CO_3$, dried ($MgSO_4$) and the solvent concentrated to give white crystalline 1,1-dioxido-2-(4-hydroxybutyl)-4,5-ethylenedioxy-1,2-benzisothiazol-3 (2H)-one, melting point 119–122° C.

Step 2: To a solution of 1,1-dioxido-2-(4-hydroxybutyl)-4,5-ethylenedioxy-1,2-benzisothiazol-3(2H)-one (313 mg, 1 mmol) and carbon tetrabromide (432 mg, 1.3 mmol) in methylene chloride (2 mL) cooled in an ice bath under a nitrogen atomosphere was added dropwise a solution of triphenylphosphine (341 mg, 1.3 mmol) in methylene chloride (3.5 mL). The reaction was allowed to stir with gradual warming to room temp. over a four hour period and then the solvent was evaporated and the residue chromatographed on a column of silica gel by elution with chloroform to give crystalline 1,1-dioxido-2-(4-bromobutyl)-4,5-ethylenedioxy-1,2-benzisothiazol-3(2H)-one from diethyl ether/hexane, melting point 135–136° C.

EXAMPLE 26

1,1-Dioxido-2-(4-(4-(3-n-propyl-2-oxo-1-benzimidazolinyl)piperidin-1-yl)pentyl)-5-chloro-1,2-benzisothiazol-3(2H)-one Starting with 4-(3-n-propyl-2-oxo-1-benzimidazolinyl) piperidine and 1,1-dioxido-2-(4-oxo-pentyl)-5-chloro-1,2-benzisothiazol-3(2H)-one and following the procedure of Example 13, the title compound is obtained.

EXAMPLE 27

1,1-Dioxido-2-(4-(4-(5-fluoro-3-(2,2,2-trifluoroethyl)-2-oxo-1-benzimidazolinyl)piperidin-1-yl)butyl)-5-chloro-1,2-benzisothiazol-3(2H)-one Hydrochloride (Compound A)

Steps 1–4 are based on modifications of procedures described by R.Henning et.al., *J.Med.Chem.* 30, 814–819 (1987):

Step 1: A solution of ethyl 4-amino-1-piperidine carboxylate (9.0 g, 52 mmol.) and 2-chloro-5-fluoronitrobenzene (10.3g, 58 mmol.) in cyclohexanol (30 mL) containing powdered sodium carbonate (6.1 g, 57 mmol.) was refluxed (>160° C.) for 30 hours or until no further reaction was indicated by tlc(30% EtOAc/hexane). (Alternatively, 2,5-difluoronitrobenzene can be used in place of the 2-chloro-5-fluoronitrobenzene). The deep reddish reaction mixture was cooled and diluted with EtOAc. This solution was washed with dil. aq. HCl (3×), water, and then the organic layer dried (anhydrous $Na_2SO_4$) and the solvent evaporated to give a red oil. This oil was flash chromatographed on a column of silica gel and the product eluted with a 10–25% EtOAc/hexane gradient. The appropriate fractions were combined, the solvents evaporated, and the residue triturated with 10% $Et_2O$/hexane to give 1-ethoxycarbonyl-4-(4-fluoro-2-nitroanilino)-piperidine as a bright reddish-orange solid, mp: 115–116° C., which was used without further purification.

Step 2: This 1-ethoxycarbonyl-4-(4-fluoro-2-nitroanilino) piperidine (5.7 g, 18.3 mmol.) was dissolved in THF (50 mL) and diluted with ethanol (100 mL). After addition of 5% platinum/carbon catalyst (1.2 g), the hydrogenation of the nitro functional group was carried out at atmospheric pressure via a balloon over a four hour period. The catalyst was removed and the solvents evaporated to give 1-ethoxycarbonyl-4-(2-amino-4-fluoroanilino)-piperidine as a viscous oil which was used as is.

Step 3: The crude 1-ethoxycarbonyl-4-(2-amino-4-fluoroanilino)piperidine above was dissolved in EtOAc (100 mL) and saturated aq. $Na_2CO_3$ (100 mL) was then added to give a two-phase system. After cooling in an ice bath, phosgene in toluene (25 mL, 1.9N) was added in portions with stirring. After one hour, the reaction mixture was warmed to room temp. and diluted with EtOAc. The organic layer was separated and washed with more $NaHCO_3$/$Na_2CO_3$ solution, dried ($Na_2SO_4$), and filtered through a pad of charcoal. The filtrate was evaporated and the residue triturated with $Et_2O$ to give purified 1-ethoxycarbonyl-4-(5-fluoro-2-oxo-1-benzimidazolinyl)piperidine as an off-white solid.

Step 4: A suspension of 1-ethoxycarbonyl-4-(5-fluoro-2-oxo-1-benzimidazolinyl)piperidine (5.22 g, 17 mmol.) in 2 N NaOH (55 mL) was refluxed for twelve hours. The clear amber solution was cooled to room temp. and solid $NH_4Cl$ (5.9 g, 110 mmol.) was added to neutralized the hydroxide. After addition of aq. $Na_2CO_3$ and 5 N NaOH (2 mL), the product was extracted into chloroform. The extract was dried ($Na_2SO_4$) and filtered through a pad of charcoal and then evaporated to give 4-(5-fluoro-2-oxo-1-benzimidazolinyl)piperidine as a pale yellow viscous oil.

Step 5: This crude 4-(5-fluoro-2-oxo-1-benzimidazolinyl) piperidine was dissolved in chloroform (70 mL), cooled in an ice bath and di-tert-butyl dicarbonate (4.13g, 19 mmol.) was added. After stirring for two hours, the solvent was evaporated and the residue triturated with $Et_2O$ to give 1-tert-butoxycarbonyl-4-(5-fluoro-2-oxo-1-benzimidazolinyl)piperidine as an off-white solid.

Step 6: Solid 1-tert-butoxycarbonyl4-(5-fluoro-2-oxo-1-benzimidazolinyl)piperidine (9.7 g, 28.9 mmol.) was dissolved in anhydrous DMF (72 mL) under an inert atmosphere and cesium carbonate (10.6 g, 32.5 mmol.) was added followed by excess 2,2,2-trifluoroethyl iodide (14.3 mL, 145 mmol.). This reaction mixture was gently warmed at 40–50° C. for an extended period (1–2 days), periodically adding additional 2,2,2-trifluoroethyl iodide (4 mL, 4 mmol in four portions) to drive the alkylation to completion. The cooled reaction mixture was diluted with EtOAc and washed with aq. $NaHCO_3$ and water (3×). The organic layer was dried ($Na_2SO_4$) and filtered through a pad of charcoal and the solvent then evaporated. The solid residue was triturated with $Et_2O$ and collected to give 1-tert-butoxycarbonyl-4-(5-fluoro-3-(2,2,2-tri-fluoroethyl)-2-oxo-1-benzimidazolinyl) piperidine as a nearly pure white solid. This material was crystallized from $CH_2Cl_2$ to remove a slightly less polar impurity affording the product, mp: 172–173° C.

Step 7: A solution of 1-tert-butoxycarbonyl-4-(5-fluoro-3-(2,2,2-trifluoroethyl)-2-oxo-1-benzimidazolinyl) piperidine (4.17 g, 10 mmol.) in chloroform (50 mL) containing trifluoroacetic acid (5.5 mL) was stirred at room temp. under an inert atmosphere for 6–12 hours until reaction was complete. The solvent and excess TFA were removed and the residue redissolved in chloroform. This solution was washed with $Na_2CO_3$/NaOH solution. The organic layer was dried ($Na_2SO_4$), filtered through a pad of charcoal, and the solvent evaporated to give 4-(5-fluoro-3-(2,2,2-trifluoroethyl)-2-oxo-1-benzimidazolinyl)piperidine as a viscous oil which was used as is. A sample of this material was converted to the HCl salt and after crystallization from methanol gave a white solid, mp: >280° C.

Step 8: The 4-(5-fluoro-3-(2,2,2-trifluoroethyl)-2-oxo-1-benzimidazolinyl)piperidine (~10 mmol.) above was dissolved in anhydrous DMF (25 mL) followed by the addition of 1,1-dioxido-2-(4-bromobutyl)-5-chloro-1,2-benzisothiazol-3(2H)-one (3.54 g, 10 mmol.) and triethylamine (1.4 mL, 10 mmol.) and allowed to stir at 50° C. under an inert atmosphere for three hours or until reaction was complete. The cooled solution was diluted with EtOAc and washed with $NaHCO_3$/$Na_2CO_3$ solutions, water (3×), and the organic layer dried ($Na_2SO_4$), filtered and the solvent evaporated to give 1,1-dioxido-2-(4-(4-(5-fluoro-3-(2,2,2-trifluoroethyl)-2-oxo-1-benzimidazolinyl)piperidin-1-yl)butyl)-5-chloro-1,2-benzisothiazol-3(2H)-one as a viscous oil. This material was dissolved in EtOAc (50 mL) and excess HCl gas/EtOAc was added to give an immediate copious white precipitate which was gently digested in the warmed EtOAc to give the crystalline HCl salt of Compound A, mp: 255–257° C. Analysis calculated for $C_{25}H_{25}ClF_4N_4O_4S \cdot HCl$: C,48.00; H,4.19; N, 8.96; found: C,47.96; H, 4.17; N, 8.93. The NMR was consistent with structure.

EXAMPLE 28

2-(4-Bromobutyl)-1,1-dioxido-5-ethoxy-1,2-benzothiazol-3(2H)-one

Using the procedures described for Example 25, but substituting ethoxybenzene for 1,4-benzodioxane, the title compound was obtained as a white crystalline compound, mp: 105–108° C.

EXAMPLE 29

1,1-Dioxido-2-(4-(4-(5-fluoro-3-(2,2,2-trifluoroethyl)-2-oxo-1-benzimidazolinyl)piperidin-1-yl)butyl)-1,2-benzisothiazol-3(2H)-one Hydrochloride (Compound F)

Using the procedures described for Example 27, but substituting 1,1-dioxido-2-(4-bromobutyl)-1,2- benzisothiazol-3(2H)-one for 1,1-dioxido-2-(4-bromobutyl)-5-chloro-1,2-benzisothiazol-3(2H)-one in step 8, the title compound was obtained as a white crystalline HCl salt, mp: 267–269° C. Analysis calculated for $C_{25}H_{26}F_4N_4O_4S.HCl$: C,50.80; H,4.61; N,9.48; found: C,50.64; H,4.56; N,9.42. The NMR was consistent with the structure.

EXAMPLE 30

1,1-Dioxido-2-(4-(4-(5-fluoro-3-(2,2,2-trifluoroethyl)-2-oxo-1-benzimidazolinyl)piperidin-1-yl)butyl)-5-ethoxy-1,2-benzisothiazol- 3(2H)-one Hydrochloride (Compound E)

Using the procedures described for Example 27, but substituting 1,1-dioxido-2-(4-bromobutyl)-5-ethoxy-1,2-benzisothiazol-3(2H)-one for 1,1-dioxido-2-(4-bromobutyl)-5-chloro-1,2-benzisothiazol-3(2H)-one in step 8, the title compound was obtained as a white crystalline HCl salt, mp: 224–225° C. Analysis calculated for $C_{27}H_{30}F_4N_4O_5S.HCl.0.6\ H_2O$: C,50.20; H,5.03; N,8.68; found: C,50.18; H,4.86; N,8.59. The NMR was consistent with the structure.

EXAMPLE 31

1,1-Dioxido-2-(4-(4-(5-fluoro-3-(2,2,2-trifluoroethyl)-2-oxo-1-benzimidazolinyl)piperidin-1-yl)butyl)-5-trifluoromethoxy-1,2-benzisothiazol-3 (2H)-one Hydrochloride (Compound G)

Using the procedures described for Example 27, but substituting 1,1-dioxido-2-(4-bromobutyl)-5-trifluoromethoxy-1,2-benzisothiazol-3(2H)-one for 1,1-dioxido-2-(4-bromobutyl)-5-chloro-1,2-3-benzisothiazol-3(2H)-one in step 8, the title compound was obtained as a white crystalline HCl salt, mp: 260–262° C. The NMR was consistent with the structure.

EXAMPLE 32

1,1-Dioxido-2-(4-(4-(5-fluoro-3-(2-fluoroethyl)-2-oxo-1-benzimidazolinyl)piperidin-1-yl)butyl)-5-chloro-1,2-benzisothiazol-3(2H)-one Hydrochloride (Compound H)

Using the procedures described for Example 27, but substituting 2-fluoroethyl bromide for 2,2,2-trifluoroethyl iodide in step 6, the title compound was obtained as a white crystalline HCl salt, mp: 259–261° C. Analysis calculated for $C_{25}H_{27}ClF_2N_4O_4S.HCl.0.45\ H_2O$: C,50.24; H,4.87; N,9.38; found: C,50.25; H,4.70; N,9.25. The NMR was consistent with the structure.

EXAMPLE 33

1,1-Dioxido-2-(4-(4-(5-methyl-3-(2,2,2-trifluoroethyl)-2-oxo-1-benzimidazolinyl)piperidin-1-yl)butyl)-5-chloro-1,2-benzisothiazol-3(2H)-one Hydrochloride (Compound B)

Using the procedures described for Example 27, but substituting 2-chloro-5-methylnitrobenzene for 2-chloro-5-fluoronitrobenzene in step 1, the title compound was obtained as a white crystalline HCl salt, mp: 245–247° C. Analysis calculated for $C_{26}H_{28}ClF_3N_4O_4S.HCl.H_2O$: C,48.90; H,4.74; N,8.78; found: C,48.93; H,4.81; N,8.84. The NMR was consistent with the structure.

EXAMPLE 34

1,1-Dioxido-2-(4-(4-(5-chloro-3-(2,2,2-trifluoroethyl)-2-oxo-1-benzimidazolinyl)piperidin-1-yl)butyl)-5-chloro-1,2-benzisothiazol-3(2H)-one Hydrochloride (Compound C)

Using the procedures described for Example 27, but substituting 2,5-dichloronitrobenzene for 2-chloro-5-fluoronitrobenzene in step 1, the title compound was obtained as a white crystalline HCl salt, mp: 251–252° C. Analysis calculated for $C_{25}H_{25}Cl_2F_3N_4O_4S.HCl.0.40\ H_2O$: C,46.25; H,4.16; N,8.63; found: C,46.28; H,4.10; N,8.48. The NMR was consistent with the structure.

EXAMPLE 35

1,1-Dioxido-2-(4-(4-(5-chloro-3-(2,2,2-trifluoroethyl)-2-oxo-1-benzimidazolinyl)piperidin-1-yl)butyl)-1,2-benzisothiazol-3(2H)-one Hydrochloride (Compound J)

Using the procedures described for Example 27, but substituting 2,5-dichloronitrobenzene for 2-chloro-5-fluoronitrobenzene in step 1 and 1,1-dioxido-2-(4-bromobutyl)-1,2-benzisothiazol-3(2H)-one for 1,1-dioxido-2-(4-bromobutyl)-5-chloro-1,2-benzisothiazol-3(2H)-one in step 8, the title compound was obtained as a white crystalline HCl salt, mp: 263–265° C. Analysis calculated for $C_{25}H_{26}ClF_3N_4O_4S.HCl.0.45\ H_2O$: C,48.77; H,4.57; N,9.10; found: C,48.79; H,4.45; N,9.05. The NMR was consistent with the structure.

EXAMPLE 36

1,1-Dioxido-2-(4-(4-(5-chloro-3-ethyl-2-oxo-1-benzimidazolinyl)piperidin-1-yl)butyl)-5-chloro-1,2-benzisothiazol-3(2H)-one Hydrochloride (Compound K)

Using the procedures described for Example 27, but substituting 2,5-dichloronitrobenzene for 2-chloro-5-fluoronitrobenzene in step 1 and ethyl iodide for 2,2,2-trifluoroethyl iodide in step 6, the title compound was obtained as a white crystalline HCl salt, mp: 243–246° C. Analysis calculated for $C_{25}H_{28}Cl_2N_4O_4S.HCl.0.75\ H_2O$: C,49.92; H,5.11; N,9.32; found: C,49.94; H,4.90; N,9.30. The NMR was consistent with the structure.

EXAMPLE 37

1,1-Dioxido-2-(4-(4-(5-chloro-3-(2-fluoroethyl)-2-oxo-1-benzimidazolinyl)piperidin-1-yl)butyl)-5-chloro-1,2-benzisothiazol-3(2H)-one Hydrochloride (Compound D)

Using the procedures described for Example 27, but substituting 2,5-dichloronitrobenzene for 2-chloro-5-fluoronitrobenzene in step 1 and 2-fluoroethyl bromide for 2,2,2-trifluoroethyl iodide in step 6, the title compound was obtained as a white crystalline HCl salt, mp: 260–261° C. Analysis calculated for $C_{25}H_7Cl_2FN_4O_4S.HCl$: C,49.55; H,4.66; N,9.25; found: C,49.78; H,4.67; N,9.27. The NMR was consistent with the structure.

EXAMPLE 38

1,1-Dioxido-2-(4-bromobutyl)-5-trifluoromethoxy-1,2-benzisothiazol-3(2H)-one

Using the procedures described for Example 25, but substituting 4-trifluoromethoxybenzenesulfonyl chloride for 6-chlorosulfonyl-1,4-benzodioxane, the title compound was obtained as a white crystalline solid, mp: 77–78° C. The NMR was consistent with the structure.

The following compounds, shown below in Tables 2–4, were prepared in the same manner as described in detail above using readily available starting materials.

TABLE 2

| $R^3$ | $R^4$ | mp(° C.) |
|---|---|---|
| H | 5-$CH_3$ | 266–270 |
| H | 4,5 —O—CH₂CH₂—O— | >170 |
| H | 5-$OCH_3$ | 236–238 |
| H | 4-$OCH_3$ | >150 |
| $CH_3$ | 5-Cl | 251–253 |

TABLE 3

| $R^1$ | $R^2$ | $R^4$ | $R^5$ |
|---|---|---|---|
| H | H | Cl | $CO_2CH_3$ cis(−) |
| H | H | Cl | $CO_2CH_3$ cis(+) |
| H | H | Cl | $CO_2CH_3$ trans(±) |
| H | 5/6-$CH_3$ ~3:1 | Cl | $CO_2CH_3$ cis(±) |
| Et | H | Cl | $CO_2CH_3$ cis(±) |
| H | 5,6-diF | Cl | $CO_2CH_3$ cis(±) |
| H | H | Cl | di-substituted with $CH_3$ and $CO_2CH_3$ |
| $CO_2Et$ | H | Cl | $CO_2CH_3$ cis(±) |
| H | H | Cl | $CO_2Et$ cis(±) |
| H | H | Cl | $CO_2CH_2Ph$ cis(±) |
| H | H | Cl | CONHEt cis(±) |
| H | H | Cl | CONHMe |

TABLE 3-continued

| $R^1$ | $R^2$ | $R^4$ | $R^5$ |
|---|---|---|---|
| H | H | Cl | $CONMe_2$ cis(±) |
| H | H | Cl | $CONH_2$ cis(±) |
| H | H | Cl | $CONHCH_2Ph$ cis(±) |
| $FCH_2CH_2$ | H | Cl | $CO_2Me$ cis (±) |
| $FCH_2CH_2$ | H | H | $CO_2Me$ cis (±) |
| H | H | H | $CO_2Et$ cis (±) |
| H | H | Cl | $CH_2OH$ cis(±) |
| $CF_3CH_2$ | H | Cl | $CH_2OH$ cis(±) |
| $CF_3CH_2$ | H | H | $CH_2OH$ cis(±) |
| $CF_3CH_2$ | 5,6-diF | Cl | $CH_2OH$ cis(±) |
| H | H | H | $CO_2CH_2Ph$ cis(±) |
| Et | H | Cl | $CH_2OH$ cis(±) |
| Et | H | H | $CH_2OH$ cis(+) |
| Et | H | H | $CH_2OPh$ cis(±) |
| H | H | H | $NH_2$ |
| H | H | H | NHCOMe cis(±) |
| H | H | Cl | $NHCO_2Et$ cis(±) |
| $CF_3CH_2$- | 5,6-diF | Cl | H |
| Ph | H | Cl | H |
| Ph | H | H | H |
| cyclohexyl | H | Cl | H |
| cyclohexyl | H | H | H |
| ICH=CF- | H | Cl | H |

TABLE 4

| $R^1$ | $R^2$ | $R^4$ | $R^5$ |
|---|---|---|---|
| Et | H | Cl | CN |
| n-Pr | H | H | CN |
| n-Pr | H | Cl | $CONH_2$ |
| n-Pr | H | H | $CONH_2$ |
| n-Pr | H | Cl | $CO_2Me$ |

The following compounds, shown below in Table 5, are prepared in the same manner as described in detail above using readily available starting materials.

TABLE 5

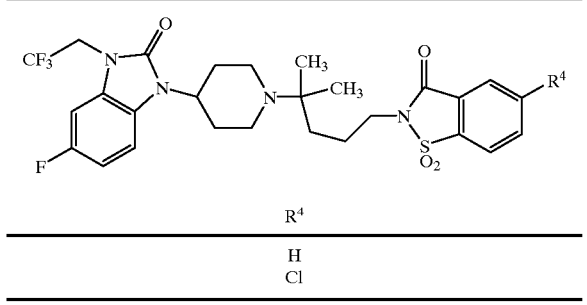

| R⁴ |
|---|
| H |
| Cl |

EXAMPLE 39

As a specific embodiment of an oral composition, 100 mg of the compound of Example 27 (i.e., Compound A) is formulated with sufficient finely divided lactose to provide a total amount of 580 to 590 mg to fill a size O hard gel capsule.

EXAMPLE 40

Screening assay: Alpha 1a Adrenergic Receptor Binding

Membranes prepared from the stably transfected human $\alpha_{1a}$ cell line (ATCC CRL 11140) were used to identify compounds that bind to the human alpha 1a adrenergic receptor. These competition binding reactions (total volume=200 ul) contained 50 mM Tris-HCl pH. 7.4, 5 mM EDTA, 150 mM NaCl, 100 pM [$^{125}$I]-HEAT, membranes prepared from the $\alpha_{1a}$ a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values ≦1 nM.

EXAMPLE 41

Selective Binding assays

Membranes prepared from stably transfected human $\alpha_{1d}$ and $\alpha_{1b}$ cell lines (ATCC CRL 11138 and CRL 11139, respectively) were used to identify compounds that selectively bind to the human alpha 1a adrenergic receptor. These competition binding reactions (total volume=200 ul) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 42

Exemplary Counterscreens

1. Assay Title: Dopamine $D_2$, $D_3$, $D_4$ in vitro screen
Objective of the Assay:

The objective of this assay is to eliminate agents which specifically affect binding of [$^3$H] spiperone to cells expressing human dopamine receptors $D_2$, $D_3$ or $D_4$.

Method:

Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 μg membranes in a total volume of 500 μl containing 0.2 nM [$^3$H]-spiperone. Non-specific binding is defined using 10 μM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a
Objective of the Assay

The objective of this assay is to eliminate agents which specifically affect binding to cloned human 5HT1a receptor
Method:

Modified from Schelegel and Peroutka Biochemical Pharmacology 35: 1943–1949 (1986).

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM $CaCl_2$ and 1 mg/ml ascorbate. Non-specific binding is defined using 10 μM propranolol. The assay is terminated after a 1 hour incubation at room temperature by rapid filtration over GF/Cfilters

EXAMPLE 43

Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/ 95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 $\mu$M (for rat), 10 $\mu$M (for dog) and 20 $\mu$M (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. pA2 (–log Kb) values were obtained from Schild plot when three or more concentrations were tested. When less than three concentrations of antagonist are tested, Kb values are calculated according to the following formula $$K_b = \frac{[B]}{x-1},$$

where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptoxantagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/g/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

EXAMPLE 44

Opioid receptor binding assay $^3$H-Naloxone binds with high affinity to opiate receptors in brain tissue (Creese and Snyder, *J. Pharm Expt. Ther.,*

194: 205–219, 1975). The potency of a compound to inhibit the specific binding of this radioligand gives a measure of the affinity for these receptors. $^3$H-Naloxone binding in rat brain membranes was performed as described by Creese and Snyder (*J. Pharm. Expt. Ther.*, 194, 205–219, 1975) using Tris buffer alone or in the presence of 150 mM NaCl. Naloxone binding for representative examples of the present invention are given below in Table 6.

TABLE 6

| Example No. | Naloxone binding (nM) |
|---|---|
| 2 | 11 ± 2.9 |
| 3 | 1.8 |
| 12 | 4.4 |
| 13 | 16 ± 1 |

EXAMPLE 45

Radioligand binding assays for opioid receptor subtypes

Opioid mu and delta receptor binding assays were performed with rat brain membranes using $^3$H-DAMGO ([D-Ala$^2$, Me-Phe$^4$, Gly-ol$^5$]enkephalin, 1 nM) and $^3$H-DPDPE ([D-Pen$^2$, D-Pen$^5$]enkephalin, 3 nM) as the selective radioligand, respectively (Slater and Cross, 1991, Methods in Neurosciences ed. P. M. Conn. Academic Press, vol. 5 pp.459–478). Kappa receptor binding assays were performed with guinea pig brain membranes using $^3$H-U69593 (5 alpha, 7 alpha, 8 beta)-(+)-N-Methyl-N-[7-(1-pyrrolinyl)-1-oxaspiro[4,5]dec-8-yl]benzene-acetamide, 5 nM) as the radioligand. Brain membrane preparation and radioligand binding assays were performed similarly to those for $^3$H-naloxone binding assay with the exception as noted below. Some protease inhibitors (bacitracin 20 μg/ml, soy-bean trypsin inhibitor 50 μg/ml and leupeptin 10 μg/ml) were added to the binding assay buffer for $^3$H-DAMGO and $^3$H-DPDPE binding assays. Binding assays were carried out at 25° C. for 1 hour ($^3$H-DAMGO and $^3$H-U69593) and 3 hours ($^3$H-DPDPE). Nonspecific binding was determined in the presence of 1 μM of naloxone. The selectivity of representative compounds of the present invention on opioid receptor subtypes are shown below in Table 7.

TABLE 7

| | IC$_{50}$ (nM) | | |
|---|---|---|---|
| Example Number | $^3$H-DAMGO (mu)$^a$ | $^3$H-DPDPE (delta)$^a$ | $^3$H-U69593 (kappa)$^b$ |
| 3 | 1.9 | 4300 | 1200 |
| 12 | 7.7 | 3000 | 490 |
| 13 | 33 | 5700 | 1700 |

$^a$,rat brain
$^b$,guinea pig brain

EXAMPLE 46

Opioid Activity in Electrically Induced Contraction of Guinea Pig Ileum

The isolated guinea pig ileum contracts to field stimulation via release of acetylcholine that can be inhibited by the activation of opiate receptors (Kosterlitz and Watt, Br. *J. Pharmacol. Chemother.*, 33, 266–276, 1968). Guinea pig ileum longitudinal muscles with attached myenteric plexus were removed by the method of Paton and Zar (*J. Physiol.*, 194, 13–33, 1968) and were mounted in organ baths (5 ml) containing Krebs-Ringer-bicarbonate solution under 0.5 g tension. The strips were stimulated by supramaximal electrical stimulation via two platinum electrodes at 0.15 Hz and 1.5 msec pulse duration. The strips were allowed to equilibrate under continuous stimulation with washes every 10 minutes until a constant base-line response was obtained. Test compounds were given cumulatively. In some studies, at the end of this cumulative dose response study, naloxone (1–10 μM) was given to determine whether the inhibition was reversible by an opiate antagonist. Opiod agonist activity of representative examples in this preparation are shown below in Table 8.

TABLE 8

| Example Number | Guunea pig ileum EC$_{50}$ (nM) | Naloxone Reversible |
|---|---|---|
| 3 | 3.8 | yes |
| 12 | 37 | yes |
| 13 | 110 | yes |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of treating a condition which is susceptible to treatment by agonism of the mu opioid receptor which comprises administering to a subject in need thereof an amount of a compound effective to treat the condition wherein the compound has the formula:

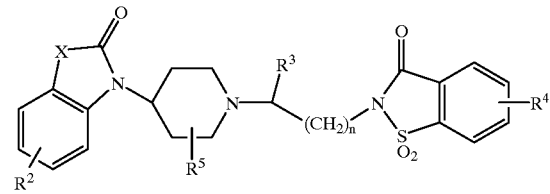

wherein

X is selected from N—R$^1$ or O;

R$^1$ is selected from the group consisting of hydrogen, C$_{3-6}$ cycloalkyl, unsubstituted or substituted C$_{1-6}$ alkyl where the substituent on the alkyl is selected from mono-, di- or tri-halogen, C$_{1-4}$ alkoxy, carboxy, CONH$_2$, SO$_2$NH$_2$, a heterocyclic ring or aryl, and unsubstituted or substituted C$_{2-6}$ alkenyl where the substituent on the alkenyl is selected from mono-, di- or tri-halogen, C$_{1-4}$ alkoxy, carboxy, CONH$_2$, SO$_2$NH$_2$, R$^2$ is independently one or more of hydrogen, halogen, C$_{1-4}$ alkoxy, mono-, di- or tri-halogenated C$_{1-4}$ alkoxy or unsubstituted or substituted C$_{1-6}$ alkyl where the substituent on the alkyl is selected from mono-, di- or tri-halogen, C$_{1-4}$ alkoxy, carboxy, CONH$_2$, SO$_2$NH$_2$, R$^3$ is selected from hydrogen, cyano, CO$_2$R$^1$, CONH$_2$, CONHR$^1$, CON(R$^1$)$_2$, C$_{3-6}$ cycloalkyl, C$_{3-6}$ cycloalkyl wherein one of the carbon atoms is replaced with a heteroatom selected from O or NH, or unsubstituted or substituted mono- or di-$C_{1-6}$ alkyl wherein the substituent on the mono- or di-alkyl is selected from hydroxy, $C_{1-4}$ alkoxy, amino or mono-, di- or tri-halogen;

$R^4$ is independently one or more of hydrogen, $C_{1-6}$ alkyl, halogen, $C_{1-4}$ alkoxy, mono-, di- or tri-halogenated $C_{1-4}$ alkoxy, nitro, amino, mono-, di- or tri-halogenated $C_{1-6}$ alkyl, $C_{1-6}$ alkylsulfonyl, $C_{1-4}$ alkylenedioxy, unsubstituted or substituted aryl where the substituent on the aryl is selected from halogen, unsubstituted $C_{1-3}$ alkyl, mono-, di- or tri-halogenated $C_{1-3}$ alkyl or $C_{1-4}$ alkoxy-$C_{1-3}$ alkyl, or unsubstituted or substituted heterocyclic ring where the substituent on the heterocyclic ring is selected from halogen, unsubstituted $C_{1-3}$ alkyl, mono-, di- or tri-halogenated $C_{1-3}$ alkyl or $C_{1-4}$ alkoxy-$C_{1-3}$ alkyl;

$R^5$ is independently one or more of hydrogen, cyano, $C_{1-6}$ alkyl, $CO_2R^1$, $CONH_2$, $CONHR^1$, $CON(R^1)_2$; and n is an integer of from 2 to 4;

and the pharmaceutically acceptable salts thereof.

2. A method of alleviating pain in a subject in need thereof which comprises administering to the subject a therapeutically effective amount of the compound of claim 1.

3. The method of alleviating pain of claim 2, wherein $R^3$ is selected from cyano, $CO_2R^1$, $CONH_2$, $CONHR^1$, $CON(R^1)_2$, $C_{3-6}$ cycloalkyl, $C_{3-6}$ cycloalkyl wherein one of the carbon atoms is replaced with a heteroatom selected from O or NH, or unsubstituted or substituted mono- or di-$C_{1-6}$ alkyl wherein the substituent on the mono- or di-alkyl is selected from hydroxy, $C_{1-4}$ alkoxy, amino or mono-, di- or tri-halogen; and $R^4$ is independently one or more of hydrogen, $C_{1-6}$ alkyl, halogen, $C_{1-4}$ alkoxy, mono-, di- or tri-halogenated $C_{1-4}$ alkoxy, nitro or $C_{1-4}$ alkylenedioxy;

and the pharmaceutically acceptable salts thereof.

4. The method of alleviating pain of claim 3, wherein $R^1$ is selected from the group consisting of hydrogen, unsubstituted or substituted $C_{1-6}$ alkyl where the substituent on the alkyl is selected from mono-, di- or tri-halogen, $C_{1-4}$ alkoxy, carboxy, $CONH_2$, a heterocyclic ring or phenyl, and unsubstituted or substituted $C_{2-6}$ alkenyl where the substituent on the alkenyl is mono-, di- or tri-halogen;

$R^2$ is independently one or more of hydrogen, halogen or $C_{1-6}$ alkyl;

$R^3$ is selected from cyano, $C_{1-4}$ alkoxycarbonyl, $CONH_2$ or unsubstituted or substituted mono- or di-$C_{1-6}$ alkyl wherein the substituent on the mono- or di-alkyl is mono-, di- or tri-halogen;

$R^4$ is independently one or more of hydrogen or halogen; and $R^5$ is independently one or more of hydrogen, cyano, $C_{1-6}$ alkyl or $CO_2R^1$;

and the pharmaceutically acceptable salts thereof.

5. The method of alleviating pain of claim 4, wherein $R^1$ is selected from hydrogen, $C_{1-6}$ alkyl, mono-, di- or tri-halogenated $C_{1-6}$ alkyl, benzyl, $C_{2-6}$ alkenyl or mono-, di- or tri-halogenated $C_{2-6}$ alkenyl;

$R^3$ is selected from cyano or mono- or di-$C_{1-6}$ alkyl; and $R^4$ is independently one or more of hydrogen or chlorine;

and the pharmaceutically acceptable salts thereof.

6. The method of alleviating pain of claim 5, wherein the compound has the formula

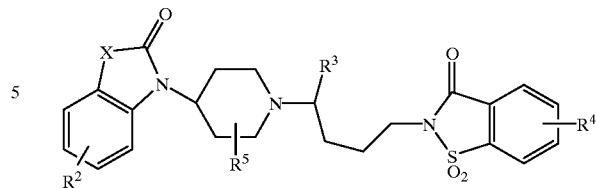

wherein $R^1$ is selected from hydrogen, $C_{1-4}$ alkyl, $C_{2-6}$ alkenyl, benzyl, trifluoroethyl or fluoroethyl;

$R^2$ is independently one or more of hydrogen, chlorine, fluorine or methyl; and $R^3$ is selected from hydrogen, methyl or dimethyl; and $R^5$ is independently one or more of hydrogen, cyano, methyl or methoxycarbonyl;

and the pharmaceutically acceptable salts thereof.

7. The method of alleviating pain of claim 6, wherein the compound has the formula

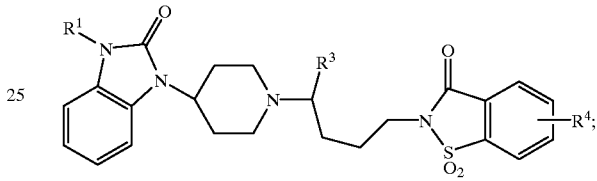

and the pharmaceutically acceptable salts thereof.

8. The method of alleviating pain of claim 7, wherein the compound is selected from the group consisting of 1,1-dioxido-2-(4-(4-(3-propyl-2-oxo-1-benzinidazolinyl)piperidin-1-yl)butyl)-5-chloro-1,2-benzisothiazol-3-(2H)-one;

1,1-dioxido-2-(4-(4-(3-ethyl-2-oxo-1-benzimidazolinyl)piperidin-1-yl)pentyl)-1,2-benzisothiazol-3(2H)-one;

1,1-dioxido-2-(4-(4-(3-ethyl-2-oxo-1-benzimidazolinyl)piperidin-1-yl)4-methylpentyl)-1,2-benzisothiazol-3(2H)-one;

1,1-dioxido-2-(4-(4-(3-ethyl-2-oxo-1-benzimidazolinyl)piperidin-1-yl)butyl)-1,2-benzisothiazol-3(2H)-one;

1,1-dioxido-2-(4-(4-(3-(2,2,2-trifluoroethyl)-2-oxo-1-benzimidazolinyl)piperidin-1-yl)butyl)-1,2-benzisothiazol-3(2H)-one;

1,1-dioxido-2-(4-(4-(3-n-propyl-2-oxo-1-benzimidazolinyl)piperidin-1-yl)butyl)-1,2-benzisothiazol-3(2H)-one;

1,1-dioxido-2-(4-(4-(3-benzyl-2-oxo-1-benzimidazolinyl)piperidin-1-yl)butyl)-1,2-benzisothiazol-3(2H)-one;

1,1-dioxido-2-(4-(4-(3-ethyl-2-oxo-1-benzimidazolinyl)piperidin-1-yl)butyl-5-chloro-1,2-benzisothiazol-3(2H)-one;

1,1-dioxido-2-(4-(4-(3-(2-fluoroethyl)-2-oxo-1-benzimidazolinyl)piperidin-1-yl)butyl-5-chloro-1,2-benzisothiazol-3(2H)-one;

1,1-dioxido-2-(4-(4-(3-ethyl-2-oxo-1-benzimidazolinyl)piperidin-1-yl)butyl)-4,5-ethylenedioxy-1,2-benzisothiazol-3(2H)-one;

1,1-dioxido-2-(4-(4-(5-methyl-3-ethyl-2-oxo-1-benzimidazolinyl)piperidin-1-yl)butyl)-5-chloro-1,2-benzisothiazol-3(2H)-one;

1,1-dioxido-2-(4-(4-(2-oxo-1-benzimidazolinyl)piperidin-1-yl)-4-methylpentyl)-1,2-benzisothiazol-3(2H)-one;

1,1-dioxido-2-(4-(4-(2-oxo-1-benzimidazolinyl)piperidin-1-yl)pentyl)-1,2-benzisothiazol-3(2H)-one;

1,1-dioxido-2-(4-(4-(3-isopropyl-2-oxo-1-benzimidazolinyl)piperidin-1-yl)butyl)-5-chloro-1,2-benzisothiazol-3(2H)-one;

1,1-dioxido-2-(4-(4-(3-butyl-2-oxo-1-benzimidazolinyl) piperidin-1-yl)butyl)-5-chloro-1,2-benzisothiazol-3(2H)-one;

1,1-dioxido-2-(4-(4-(3-(2,2,2-trifluoroethyl)-2-oxo-1-benzimidazolinyl)piperidin-1-yl)butyl)-5-chloro-1,2-benzisothiazol-3(2H)-one;

1,1-dioxido-2-(4-(4-(2-oxo-3-benzoxazolinyl)piperidin-1-yl)pentyl)-1,2-benzisothiazol-3(2H)-one;

1,1-dioxido-2-(4-(4-(6-methyl-2-oxo-3-benzoxazolinyl) piperidin-1-yl)pentyl)-1,2-benzisothiazol-3(2H)-one;

1,1-dioxido-2-(4-(4-(-2-oxo-3-benzoxazolinyl)-2-methylpiperidin-1-yl)butyl)-1,2-benzisothiazol-3(2H)-one;

1,1-dioxido-2-(4-(4-(2-oxo-1-benzimidazolinyl)-3-methoxycarbonylpiperidin-1-yl)butyl)-5-chloro-1,2-benzisothiazol-3(2H)-one;

1,1-dioxido-2-(4-(4-(5-fluoro-3-ethyl-2-oxo-1-benzimidazolinyl)piperidin-1-yl)butyl)-5-chloro-1,2-benzisothiazol-3(2H)-one;

1,1-dioxido-2-(4-(2-cyano-4-(3-propyl-2-oxo-1-benzimidazolinyl) piperidin-1-yl)butyl)-5-chloro-1,2-benzisothiazol-3(2H)-one; and 1,1-dioxido-2-(4-(4-(3-n-propyl-2-oxo-1-benzimidazolinyl) piperidin-1-yl)pentyl)-5-chloro-1,2-benzisothiazol-3 (2H)-one;

and the pharmaceutically acceptable salts thereof.

9. The method of alleviating pain of claim 8, wherein the compound is selected from 1,1-dioxido-2-(4-(4-(2-oxo-1-benzimidazolinyl)piperidin-1-yl)pentyl)-1,2-benzisothiazol-3(2H)-one;

1,1-dioxido-2-(4-(4-(3-ethyl-2-oxo-1-benzimidazolinyl) piperidin-1-yl)pentyl)-1,2-benzisothiazol-3(2H)-one;

1,1-dioxido-2-(4-(4-(3-n-propyl-2-oxo-1-benzimidazolinyl) piperidin-1-yl)pentyl)-5-chloro-1,2-benzisothiazol-3 (2H)-one;

1,1-dioxido-2-(4-(4-(3-ethyl-2-oxo-1-benzimidazolinyl) piperidin-1-yl)4-methylpentyl)-1,2-benzisothiazol-3 (2H)-one; or 1,1-dioxido-2-(4-(4-(2-oxo-1-benzimidazolinyl)piperidin-1-yl)-4-methylpentyl)-1,2-benzisothiazol-3(2H)-one;

and the pharmaceutically acceptable salts thereof.

10. The method of alleviating pain of claim 9, wherein the compound is selected from 1,1-dioxido-2-(4-(4-(3-ethyl-2-oxo-1-benzimidazolinyl) piperidin-1-yl)4-methylpentyl)-1,2-benzisothiazol-3 (2H)-one;

1,1-dioxido-2-(4-(4-(2-oxo-1-benzimidazolinyl)piperidin-1-yl)-4-methylpentyl)-1,2-benzisothiazol-3(2H)-one; or 1,1-dioxido-2-(4-(4-(3-ethyl-2-oxo-1-benzimidazolinyl) piperidin-1-yl)pentyl)-1,2-benzisothiazol-3(2H)-one;

and the pharmaceutically acceptable salts thereof.

11. A method of inducing analgesia in a subject in need thereof which comprises administering to the subject a therapeutically effective amount of the compound of claim 1.

12. The method of inducing analgesia of claim 11, wherein $R^3$ is selected from cyano, $CO_2R^1$, $CONH_2$, $CONHR^1$, $CON(R^1)_2$, $C_{3-6}$ cycloalkyl, $C_{3-6}$ cycloalkyl wherein one of the carbon atoms is replaced with a heteroatom selected from O or NH, or unsubstituted or substituted mono- or di-$C_{1-6}$ alkyl wherein the substituent on the mono- or di-alkyl is selected from hydroxy, $C_{1-4}$ alkoxy, amino or mono-, di- or tri-halogen; and $R^4$ is independently one or more of hydrogen, $C_{1-6}$ alkyl, halogen, $C_{1-4}$ alkoxy, mono-, di- or tri-halogenated $C_{1-4}$ alkoxy, nitro or $C_{1-4}$ alkylenedioxy.

13. The method of inducing analgesia of claim 12, wherein $R^1$ is selected from the group consisting of hydrogen, unsubstituted or substituted $C_{1-6}$ alkyl where the substituent on the alkyl is selected from mono-, di- or tri-halogen, $C_{1-4}$ alkoxy, carboxy, $CONH_2$, a heterocyclic ring or phenyl, and unsubstituted or substituted $C_{2-6}$ alkenyl where the substituent on the alkenyl is mono-, di- or tri-halogen;

$R^2$ is independently one or more of hydrogen, halogen or $C_{1-6}$ alkyl;

$R^3$ is selected from cyano, $C_{1-4}$ alkoxycarbonyl, $CONH_2$ or unsubstituted or substituted mono- or di-$C_{1-6}$ alkyl wherein the substituent on the mono- or di-alkyl is mono-, di- or tri-halogen;

$R^4$ is independently one or more of hydrogen or halogen; and $R^5$ is independently one or more of hydrogen, cyano, $C_{1-6}$ alkyl or $CO_2R^1$;

and the pharmaceutically acceptable salts thereof.

14. The method of inducing analgesia of claim 13, wherein $R^1$ is selected from hydrogen, $C_{1-6}$ alkyl, mono-, di- or tri-halogenated $C_{1-6}$ alkyl, benzyl, $C_{2-6}$ alkenyl or mono-, di- or tri-halogenated $C_{2-6}$ alkenyl;

$R^3$ is selected from cyano or mono- or di-$C_{1-6}$ alkyl; and $R^4$ is independently one or more of hydrogen or chlorine;

and the pharmaceutically acceptable salts thereof.

15. The method of inducing analgesia of claim 14, wherein the compound has the formula

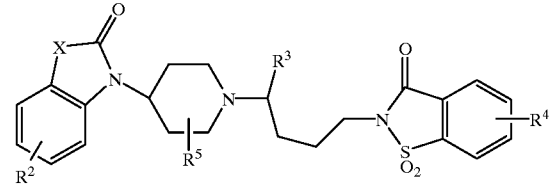

wherein $R^1$ is selected from hydrogen, $C_{1-4}$ alkyl, $C_{2-6}$ alkenyl, benzyl, trifluoroethyl or fluoroethyl;

$R^2$ is independently one or more of hydrogen, chlorine, fluorine or methyl; and $R^3$ is selected from hydrogen, methyl or dimethyl; and $R^5$ is independently one or more of hydrogen, cyano, methyl or methoxycarbonyl;

and the pharmaceutically acceptable salts thereof.

16. The method of inducing analgesia of claim 15, wherein the compound has the formula and the pharmaceutically acceptable salts thereof.

17. The method of inducing analgesia of claim 16, wherein the compound is selected from the group consisting of 1,1-dioxido-2-(4-(4-(3-propyl-2-oxo-1-benzimidazolinyl) piperidin-1-yl)butyl)-5-chloro-1,2-benzisothiazol-3-(2H)-one;

1,1-dioxido-2-(4-(4-(3-ethyl-2-oxo-1-benzimidazolinyl)
piperidin-1-yl)pentyl)-1,2-benzisothiazol-3(2H)-one;

1,1-dioxido-2-(4-(4-(3-ethyl-2-oxo-1-benzimidazolinyl)
piperidin-1-yl)4-methylpentyl)-1,2-benzisothiazol-3
(2H)-one;

1,1-dioxido-2-(4-(4-(3-ethyl-2-oxo-1-benzimidazolinyl)
piperidin-1-yl)butyl)-1,2-benzisothiazol-3(2H)-one;

1,1-dioxido-2-(4-(4-(3-(2,2,2-trifluoroethyl)-2-oxo-1-benzimidazolinyl)piperidin-1-yl)butyl)-1,2-benzisothiazol-3(2H)-one;

1,1-dioxido-2-(4-(4-(3-n-propyl-2-oxo-1-benzimidazolinyl)
piperidin-1-yl)butyl)-1,2-benzisothiazol-3(2H)-one;

1,1-dioxido-2-(4-(4-(3-benzyl-2-oxo-1-benzimidazolinyl)
piperidin-1-yl)butyl)-1,2-benzisothiazol-3(2H)-one;

1,1-dioxido-2-(4-(4-(3-ethyl-2-oxo-1-benzimidazolinyl)
piperidin-1-yl)butyl-5-chloro-1,2-benzisothiazol-3(2H)-one;

1,1-dioxido-2-(4-(4-(3-(2-fluoroethyl)-2-oxo-1-benzimidazolinyl)piperidin-1-yl)butyl-5-chloro-1,2-benzisothiazol-3(2H)-one;

1,1-dioxido-2-(4-(4-(3-ethyl-2-oxo-1-benzimidazolinyl)
piperidin-1-yl)butyl)-4,5-ethylenedioxy-1,2-benzisothiazol-3(2H)-one;

1,1-dioxido-2-(4-(4-(5-methyl-3-ethyl-2-oxo-1-benzimidazolinyl)piperidin-1-yl)butyl)-5-chloro-1,2-benzisothiazol-3(2H)-one;

1,1-dioxido-2-(4-(4-(2-oxo-1-benzimidazolinyl)piperidin-1-yl)-4-methylpentyl)-1,2-benzisothiazol-3(2H)-one;

1,1-dioxido-2-(4-(4-(2-oxo-1-benzimidazolinyl)piperidin-1-yl)pentyl)-1,2-benzisothiazol-3(2H)-one;

1,1-dioxido-2-(4-(4-(3-isopropyl-2-oxo-1-benzimidazolinyl)piperidin-1-yl)butyl)-5-chloro-1,2-benzisothiazol-3(2H)-one;

1,1-dioxido-2-(4-(4-(3-butyl-2-oxo-1-benzimidazolinyl)
piperidin-1-yl)butyl)-5-chloro-1,2-benzisothiazol-3(2H)-one;

1,1-dioxido-2-(4-(4-(3-(2,2,2-trifluoroethyl)-2-oxo-1-benzimidazolinyl)piperidin-1-yl)butyl)-5-chloro-1,2-benzisothiazol-3(2H)-one;

1,1-dioxido-2-(4-(4-(2-oxo-3-benzoxazolinyl)piperidin-1-yl)pentyl)-1,2-benzisothiazol-3(2H)-one;

1,1-dioxido-2-(4-(4-(6-methyl-2-oxo-3-benzoxazolinyl)
piperidin-1-yl)pentyl)-1,2-benzisothiazol-3(2H)-one;

1,1-dioxido-2-(4-(4-(-2-oxo-3-benzoxazolinyl)-2-methylpiperidin-1-yl)butyl)-1,2-benzisothiazol-3(2H)-one;

1,1-dioxido-2-(4-(4-(2-oxo-1-benzimidazolinyl)-3-methoxycarbonylpiperidin-1-yl)butyl)-5-chloro-1,2-benzisothiazol-3(2H)-one;

1,1-dioxido-2-(4-(4-(5-fluoro-3-ethyl-2-oxo-1-benzimidazolinyl)piperidin-1-yl)butyl)-5-chloro-1,2-benzisothiazol-3(2H)-one;

1,1-dioxido-2-(4-(2-cyano-4-(3-propyl-2-oxo-1-benzimidazolinyl) piperidin-1-yl)butyl)-5-chloro-1,2-benzisothiazol-3(2H)-one; and 1,1-dioxido-2-(4-(4-(3-n-propyl-2-oxo-1-benzimidazolinyl)
piperidin-1-yl)pentyl)-5-chloro-1,2-benzisothiazol-3
(2H)-one;

and the pharmaceutically acceptable salts thereof.

18. The method of inducing analgesia of claim 17, wherein the compound is selected from 1,1-dioxido-2-(4-(4-(2-oxo-1-benzimidazolinyl)piperidin-1-yl)pentyl)-1,2-benzisothiazol-3(2H)-one;

1,1-dioxido-2-(4-(4-(3-ethyl-2-oxo-1-benzimidazolinyl)
piperidin-1-yl)pentyl)-1,2-benzisothiazol-3(2H)-one;

1,1-dioxido-2-(4-(4-(3-n-propyl-2-oxo-1-benzimidazolinyl)
piperidin-1-yl)pentyl)-5-chloro-1,2-benzisothiazol-3
(2H)-one;

1,1-dioxido-2-(4-(4-(3-ethyl-2-oxo-1-benzimidazolinyl)
piperidin-1-yl)4-methylpentyl)-1,2-benzisothiazol-3
(2H)-one; or 1,1-dioxido-2-(4-(4-(2-oxo-1-benzimidazolinyl)piperidin-1-yl)-4-methylpentyl)-1,2-benzisothiazol-3(2H)-one;

and the pharmaceutically acceptable salts thereof.

19. The method of inducing analgesia of claim 18, wherein the compound is selected from 1,1-dioxido-2-(4-(4-(3-ethyl-2-oxo-1-benzimidazolinyl)
piperidin-1-yl)4-methylpentyl)-1,2-benzisothiazol-3
(2H)-one;

1,1-dioxido-2-(4-(4-(2-oxo-1-benzimidazolinyl)piperidin-1-yl)-4-methylpentyl)-1,2-benzisothiazol-3(2H)-one; or 1,1-dioxido-2-(4-(4-(3-ethyl-2-oxo-1-benzimidazolinyl)
piperidin-1-yl)pentyl)-1,2-benzisothiazol-3(2H)-one;

and the pharmaceutically acceptable salts thereof.

* * * * *